US012165773B2

United States Patent
Attia et al.

(10) Patent No.: US 12,165,773 B2
(45) Date of Patent: Dec. 10, 2024

(54) MACHINE-LEARNING FOR PROCESSING LEAD-INVARIANT ELECTROCARDIOGRAM INPUTS

(71) Applicant: Mayo Foundation for Medical Education and Research, Rochester, MN (US)

(72) Inventors: Itzhak Zachi Attia, Rochester, MN (US); Paul A. Friedman, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 18/440,414

(22) Filed: Feb. 13, 2024

(65) Prior Publication Data

US 2024/0266071 A1 Aug. 8, 2024

Related U.S. Application Data

(63) Continuation of application No. PCT/US2022/040362, filed on Aug. 15, 2022.

(60) Provisional application No. 63/357,312, filed on Jun. 30, 2022, provisional application No. 63/233,107, filed on Aug. 13, 2021.

(51) Int. Cl.
*A61B 5/00* (2006.01)
*A61B 5/349* (2021.01)
*G06N 3/048* (2023.01)
*G16H 50/70* (2018.01)

(52) U.S. Cl.
CPC ............. *G16H 50/70* (2018.01); *A61B 5/349* (2021.01); *G06N 3/048* (2023.01)

(58) Field of Classification Search
CPC .......... A61B 5/349–366; A61B 5/7264; A61B 5/7267; G16H 50/70
See application file for complete search history.

(56) References Cited

U.S. PATENT DOCUMENTS

| 11,763,449 B2 * | 9/2023 | Masuda | G16H 40/63 |
| | | | 600/386 |
| 2017/0366543 A1 | 12/2017 | Wang et al. | |
| 2018/0374213 A1 | 12/2018 | Arnold et al. | |
| 2019/0328243 A1 * | 10/2019 | Nemati | A61B 5/318 |
| 2022/0233129 A1 * | 7/2022 | Liu | A61B 5/7267 |

FOREIGN PATENT DOCUMENTS

WO 2023019022 A1 2/2023

OTHER PUBLICATIONS

Chen et al, 'A cascaded classifier for multi-lead ECG based on feature fusion', 2019, Computer Methods and Programs in Biomedicine, pp. 135-143. (Year: 2019).*
International Search Report; PCT/US2022/040362; Date: Dec. 29, 2022; By: Authorized Officer Kari Rodriquez.

(Continued)

*Primary Examiner* — Scott M. Getzow
(74) *Attorney, Agent, or Firm* — Caldwell Intellectual Property Law

(57) ABSTRACT

Provided herein are methods, systems, and computer program products for the detection and evaluation of cardiac condition in a lead-invariant manner.

19 Claims, 24 Drawing Sheets

(56) References Cited

OTHER PUBLICATIONS

Chen et al., A Cascaded Classifier for Multi-Lead ECG Based on Feature Fusion:. In: Computer Methods and Programs in Biomedicine 178 (Jun. 20, 2019) 135-143, https://pubmed.ncbi.nlm.nih.gov/31416542/.

Rakin AS, He Z, Fan D. Parametric noise injection: trainable randomness to improve deep neural network robustness against adversarial attack. In: 2019 IEEE/CVF Conference on Computer Vision and Pattern Recognition (CVPR). 2019, pp. 588-597.

Lecun Y, Boser B, Denker JS, Henderson D, Howard RE, Hubbard W, and Jackel LD. Backpropagation applied to handwritten zip code recognition. Neural Comput1989;1:541-551.

Lecuny, Huang FJ, Bottou L. Learning methods for generic object recognition with invariance to pose and lighting. In: Proceedings of the 2004 IEEE Computer Society Conference on Computer Vision and Pattern Recognition. Washington, DC, USA: IEEE Computer Society; 2004, pp. 97-104.

Attia ZI, et al. Screening for cardiac contractile dysfunction using an artificial intelligence-enabled electrocardiogram. Nat Med 2019;25:70-74.

Poplin R, Poplin R, Varadarajan AV, Blumer K, Liu Y, McConnell MV, Corrado GS, Peng L and Webster DR et al. Prediction of cardiovascular risk factors from retinal fundus photographs via deep learning. Nat Biomed Eng2018;2:158.

Zech Jr, Zech JR, Badgeley MA, Liu M, Costa AB, Titano JJ and Oermann EKet al. Variable generalization performance of a deep learning model to detect pneumonia in chest radiographs: a cross-sectional study. PLoS Med2018;15:e1002683-e1002683.

Narodytska N, Kasiviswanathan S. Simple black-box adversarial attacks on deep neural networks. In: 2017 IEEE Conference on Computer Vision and Pattern Recognition Workshops (CVPRW). 2017, pp. 1310-1318.

Lecun Y, Bottou L, Bengio Y, Haffner P. Gradient-based learning applied to document recognition. Proc IEEE1998;86:2278-2324.

Han X, Hu Y, Foschini L, Chinitz L, Jankelson L and Ranganath R Deep learning models for electrocardiograms are susceptible to adversarial attack. Nat Med2020;26:360-363.

Barold SS. Willem Einthoven and the birth of clinical electrocardiogramdred years ago. Card Electrophysiol Rev2003;7:99-104.

Fisch C. Evolution of the clinical electrocardiogram. Card Electrophysiol Rev2003;7: 99-104.

Becker DE. Fundamentals of electrocardiogramterpretation. Anesth Prog2006;53:53-64.

Robb GP, Marks HH. Postexercise electrocardiogram in arteriosclerotic heart disease: its value in diagnosis and prognosis. JAMA1967;200:918-926.

Wellens HJ, Bär FW, Lie K. The value of the electrocardiogram in the differential diagnosis of a tachycardia with a widened QRS complex. Am J Med 1978, 64: 27-33.

Blackburn H., Keys A., Simonson E., Rautaharju P., Punsar S. The electrocardiogram in population studies: a classification system. Circulation1960;21:1160-1175.

Attia ZI, DeSimone CV, Dillon JJ, Sapir Y, Somers VK, Dugan JL, Bruce CJ, Ackerman MJ, Asirvatham SJ, Striemer BL, Bukartyk J, Scott CG, Bennet KE, Ladewig DJ, Gilles EJ, Sadot D, Geva AB and Friedman PA et al. Novel bloodless potassium determination using a signal-processed single-lead ECG. J Am Heart Assoc2016;5:e002746.

Jesus S, Rix H. High resolution ECG analysis by an improved signal averaging method and comparison with a beat-to-beat approach. J Biomed Eng1988;10:25-32.

Karpagachelvi S, Arthanari M, Sivakumar M. ECG Feature Extraction Techniques—A Survey Approach. Int J Comput Sci Inf Secur2010;8: 76-80.

Attia ZI, et al. Age and sex estimation using artificial intelligence from standard 12-lead ECGs. Circ Arrhythm Electrophysiol2019;12:e007284.

Lawrence S, Giles CL, Tsoi AC, Back AD. Face recognition: a convolutional neural-network approach. IEEE Trans Neural Netw1997;8:98-113.

Garson A. How to measure the QT interval—what is normal? Am J Cardiol 1993;72:B14-B16.

Stewart D, Love W. A general canonical correlation index. Psychol Bull1968;70:160.

Wold S, Esbensen K, Geladi P. Principal component analysis. Chemometr Intell Lab Syst1987;2:37-52.

DeSouza IS, Sinert R. Is experienced physician gestalt with an electrocardiogram sufficient to accurately exclude acute myocardial infarction in a patient with suspected acute coronary syndrome? Acad Emerg Med 2020;27:83-84.

Wang B, Yuan B, Shi Z, Osher S. EnResNet: ResNet ensemble via the Feynman-Kac formalism to improve deep neural network robustness. Adv Neural Inf Process Syst2019;32.

* cited by examiner

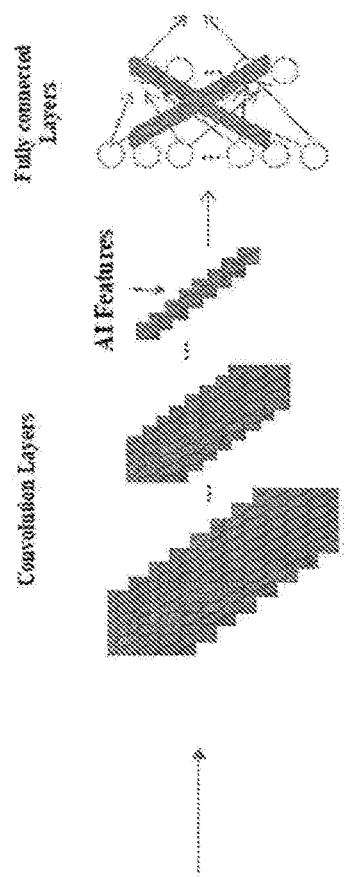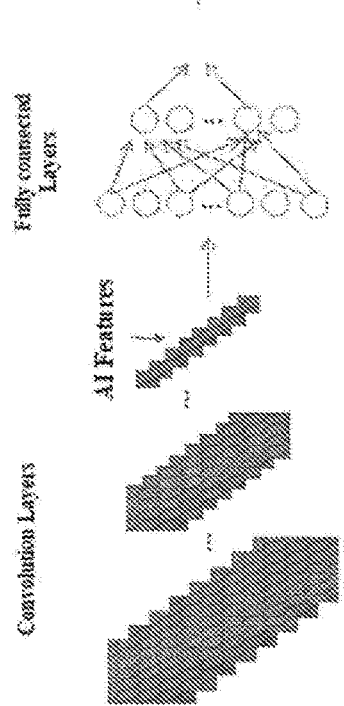
Fig. 5

2000 

| Feature name | Highest $R^2$ among leads | Lead with the highest $R^2$ | $R^2$ of average feature among leads |
|---|---|---|---|
| Based on the age network | | | |
| Average RR interval | 0.835 | | 0.835 |
| Max R amplitude | 0.824 | avL | 0.800 |
| Max S amplitude | 0.805 | III | 0.746 |
| R-wave peak amplitude | 0.803 | I | 0.789 |
| QRS complex area | 0.777 | III | 0.778 |
| T-wave peak amplitude | 0.774 | I | 0.742 |
| T-wave area | 0.766 | I | 0.729 |
| T-wave full area | 0.763 | I | 0.725 |
| R-wave area | 0.756 | I | 0.727 |
| P-wave full area | 0.729 | avR | 0.662 |
| P-wave area | 0.725 | avR | 0.663 |
| QRS complex duration | 0.670 | | 0.670 |
| P-wave peak amplitude | 0.658 | avR | 0.496 |
| S-wave peak amplitude | 0.654 | avL | 0.616 |
| QT interval | 0.620 | | 0.620 |
| S-wave area | 0.596 | V5 | 0.634 |
| P-wave duration | 0.573 | avR | 0.589 |
| R-wave duration | 0.553 | avL | 0.469 |
| QTc interval (corrected by Bazzet) | 0.548 | | 0.548 |
| S-wave duration | 0.545 | V6 | 0.471 |
| Q-wave area | 0.443 | avR | 0.433 |
| PR interval | 0.429 | | 0.429 |
| Q peak amplitude | 0.412 | I | 0.363 |
| Q-wave duration | 0.411 | avR | 0.409 |
| T-wave duration | 0.248 | avR | 0.294 |
| Based on the sex network | | | |
| Max R amplitude | 0.862 | V4 | 0.840 |
| Max S amplitude | 0.855 | avR | 0.759 |
| R-wave peak amplitude | 0.852 | V4 | 0.833 |
| R-wave area | 0.840 | V4 | 0.784 |
| Average RR interval | 0.818 | | 0.818 |
| T-wave peak amplitude | 0.794 | I | 0.809 |
| QRS complex area | 0.783 | V4 | 0.800 |
| T-wave full area | 0.780 | I | 0.775 |
| T-wave area | 0.779 | I | 0.777 |
| QRS complex duration | 0.753 | | 0.753 |
| P-wave full area | 0.679 | avR | 0.646 |
| P-wave area | 0.676 | avR | 0.643 |
| S-wave peak amplitude | 0.651 | V4 | 0.628 |
| P-wave peak amplitude | 0.606 | I | 0.509 |
| QT interval | 0.604 | | 0.604 |
| S-wave area | 0.590 | V4 | 0.633 |
| QTc interval (corrected by Bazzet) | 0.581 | | 0.581 |
| R-wave duration | 0.559 | V3 | 0.465 |
| P-wave duration | 0.523 | V4 | 0.541 |
| S-wave duration | 0.516 | V6 | 0.459 |
| Q-wave area | 0.414 | avR | 0.441 |
| Q-wave duration | 0.379 | avR | 0.398 |
| PR interval | 0.368 | | 0.368 |
| Q peak amplitude | 0.364 | I | 0.359 |
| T-wave duration | 0.255 | avR | 0.313 |

Fig. 20

MACHINE-LEARNING FOR PROCESSING LEAD-INVARIANT ELECTROCARDIOGRAM INPUTS

CROSS-REFERENCE TO RELATED APPLICATIONS

This application is a continuation of International Application No. PCT/US2022/040362, filed on Aug. 15, 2022, entitled "MACHINE-LEARNING FOR PROCESSING LEAD-INVARIANT ELECTROCARDIOGRAM INPUTS" which claims the benefit of priority of U.S. Provisional Application No. 63/233,107, filed Aug. 13, 2021, and U.S. Provisional Application No. 63/357,312, filed Jun. 30, 2022, each of which are hereby incorporated by reference in their entirety.

BACKGROUND

Electrical activity of the heart can be recorded by an electrocardiogram ("ECG"). Electrocardiograms are obtained by establishing contact between one or more electrodes and the skin or surface of an individual. In a conventional 12-lead ECG, ten electrodes are placed on an individual's chest and limbs in a known configuration, and the electrical potential between twelve pairs of the electrodes are measured and recorded. Each pair of electrodes reflects the electrical activity in a different direction on the individual's body and are commonly referred to as leads. Some ECG systems capture signals from fewer than 12 leads. For example, patches and other devices have been developed that include just a single electrode, two electrodes, or otherwise fewer than the ten electrodes provided in a 12-lead ECG configuration.

SUMMARY OF THE DISCLOSURE

In various embodiments, a system is provided for performing a machine learning task on a neural network input derived from electrocardiogram (ECG) data to generate a neural network output, the neural network input including representations of any number n of ECG leads from the ECG data in which n is an integer in the set of integers from 1 to a pre-defined maximum number of ECG leads m, the system comprising one or more computers and one or more storage devices storing instructions that, when executed by the one or more computers, cause the one or more computers to perform one or more operations to implement a neural network configured to perform the machine learning task. The neural network comprises: (i) a feature extraction sub-neural network that is configured to process the neural network input to generate n feature extraction network outputs, each of the n feature extraction network outputs describing temporal features from a different one of the n ECG leads represented in the neural network input; (ii) a feature fusing sub-neural network that is configured to process the n feature extraction network outputs generated by the feature extraction sub-neural network to generate a fused feature network output; and (iii) a task sub-neural network that is configured to process the fused feature network output to generate the neural network output.

In some embodiments, the feature extraction sub-neural network comprises one or more convolutional neural network layers configured to extract convolutional features from the neural network input.

In some embodiments, the feature extraction sub-neural network is configured to apply one or more non-linear feature extraction functions to the convolutional features extracted from the neural network input to extract the temporal features.

In some embodiments, the feature fusing sub-neural network is configured to apply a global mean or max pooling function to the n feature extraction network outputs generated by the feature extraction sub-neural network for the n ECG leads.

In some embodiments, the task-sub neural network comprises one or more attention neural network layers.

In some embodiments, the task-sub neural network comprises an output neural network layer that generates the neural network output.

In some embodiments, the output neural network layer is configured to apply a nonlinear activation function to a layer input to the output neural network layer to generate the neural network output.

In some embodiments, the ECG data collected by using each ECG lead comprises analog data characterizing ECG signals.

In some embodiments, the ECG data collected by using each ECG lead comprises numerical data comprising numerical values specifying amplitudes of the ECG signals.

In some embodiments, the ECG data collected by using each ECG lead comprises image data characterizing the ECG signals.

In some embodiments, the image data characterizing the ECG signals is in pixel format, including TIFF, PNG, or PDF file type.

In some embodiments, the machine learning task is a classification task over a set of cardiovascular diseases.

In some embodiments, the machine learning task is a regression task.

In some embodiments, the regression task is task for predicting ejection fraction readings or an individual's age, sex or race.

In some embodiments, the machine learning task is a generative task for generating text or numerical data that characterizes the ECG data.

In various embodiments, a method of training any of the foregoing neural networks is provided. A training input is derived from ECG signals. The training input is processed using the neural network in accordance with current values of a plurality of parameters of the neural network to generate a training neural network output. An update to the current values of the plurality of parameters of the neural network is determined based on optimizing an objective function for the machine learning task.

In various embodiments, one or more computer storage media are provided storing instructions that when executed by one or more computer cause the one or more computer to implement any of the foregoing neural networks.

In various embodiments, a method for using any of the foregoing neural network is provided to perform a machine learning task on a plurality of neural network inputs derived from different electrocardiogram (ECG) data to generate a neural network output, wherein the method comprises, for each of the plurality of neural network inputs: processing the neural network input using the feature extraction sub-neural network and the feature fusing sub-neural network to generate a respective fused feature network output; determining a combined intermediate neural network output based on the respective fused feature network outputs; and processing the combined intermediate neural network output using the output neural network layer of the task-sub neural network to generate the neural network output.

BRIEF DESCRIPTION OF THE DRAWINGS

FIG. 5 depicts an exemplary invariant model architecture according to embodiments of the present disclosure.

FIG. 20 is a table for $R^2$ statistic as a measure of variance explainability for single human features in the two networks according to embodiments of the present disclosure.

DETAILED DESCRIPTION

Figure 1:
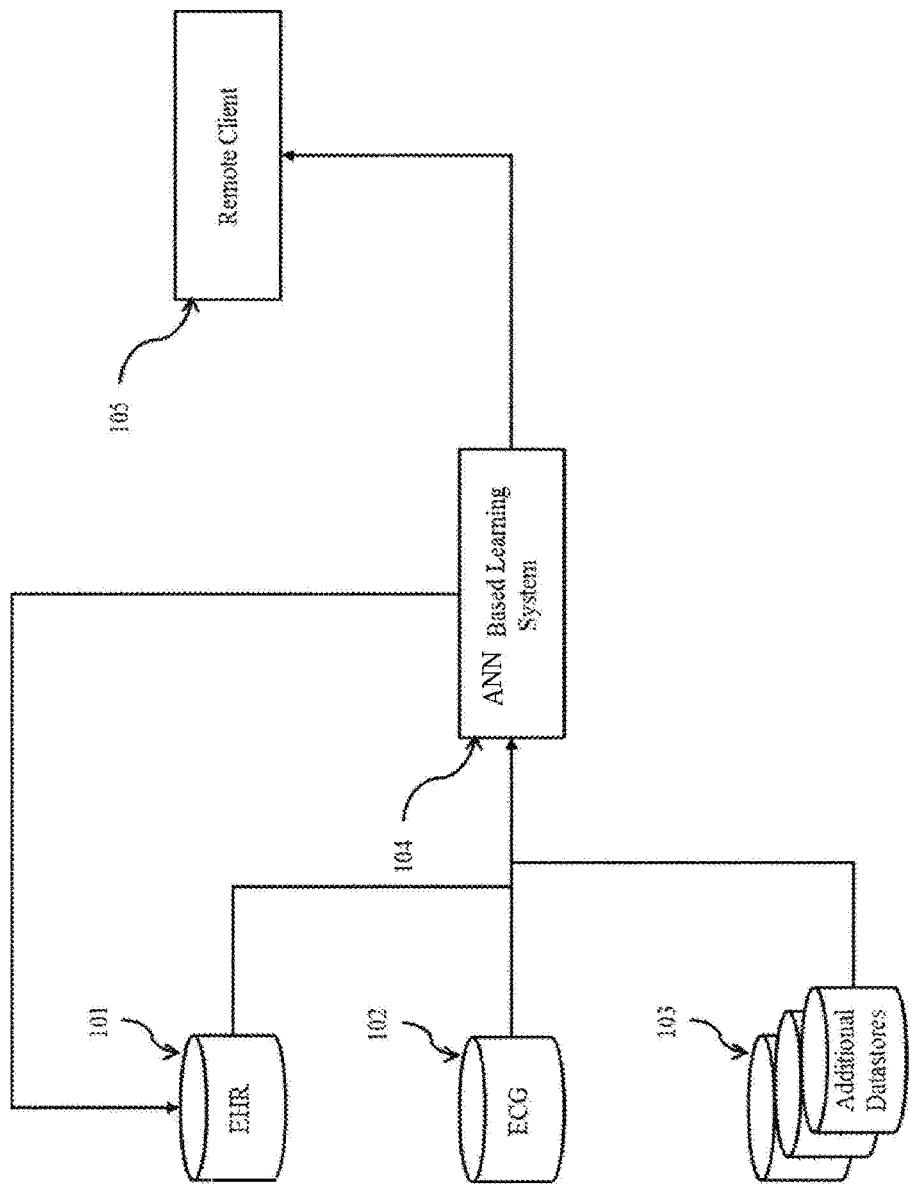
FIG. 1 is a schematic view of a system for detecting or otherwise predicting a cardiac condition according to embodiments of the present disclosure.

The present disclosure provides for the use of artificial intelligence-enabled ECG to detect cardiac condition using any single lead. Exemplary cardiac conditions discussed herein include left ventricular dysfunction and sex.

Application of artificial intelligence to the 12 lead ECG (AI ECG) identifies physiologic and pathologic conditions beyond those recognizable by expert human reviewers. A system that can process signals independent of the lead position or number of leads (lead invariant) would empower wearable ECGs in novel form factors.

The present disclosure describes that purpose-built deep neural networks (DNNs) can identify lead-invariant features from any ECG lead. In the examples below, the ability of a DNN to predict a patient's sex and the presence of left ventricular dysfunction (EF<35%) from any single lead is assessed.

In various embodiments, the DNN consists of a convolutional neural network following fully connected layers. A loss function of the models is provided considering the feature representation from the convolutional network, the output value from the fully connected layers, and the final predicted value. The networks were trained using 12-lead median ECG beats excluding lead III, aVF, aVR, and aVL from 44,995 patients (35,996 for training and 8,999 for validation) to predict low EF and sex, then evaluated on hold-out set of 52,901 patients. These results are compared to those from lead specific models trained for each lead.

For low EF classification, the area under the curve (AUC) averaged across all leads for the lead invariant model was 0.86±0.01 and the $R^2$ 0.87±0.03. When lead specific models were applied to each lead and then averaged, the AUC was 0.86±0.01 and the $R^2$ 0.43±0.13. For sex classification, the lead invariant model's average AUC was 0.81±0.02 and the averaged $R^2$ 0.72±0.08, whereas for the lead specific models, the averaged AUC and $R^2$ were 0.79±0.03 and 0.3±0.13, respectively.

Regardless of which lead is used as an input, a lead invariant model identifies ventricular dysfunction and sex effectively, in contrast to lead specific models. The lead invariant model may facilitate use of the AI ECG in mobile, portable and wearable applications.

Identification of individuals, including asymptomatic individuals, at greater risk of experiencing future cardiovascular events is critical for the implementation of preventive strategies. However, acquisition and analysis of cardiac data is often performed by computed tomography which is expensive, requires highly specialized equipment and trained technicians, not readily accessible, and exposes the individual to radiation. Accordingly, the invention provided herein is based, at least in part, on a deep learning (DL) algorithm designed and developed to detect cardiac conditions based on electrocardiogram inputs.

Convolutional neural networks offer a comprehensive approach to analyzing and interpreting the vast amount of data generated in a single ECG. Because smartphone-enabled electrodes permit point-of-care diagnosis with single-lead and 6-lead options, the methods described herein are applicable to a broad array of both consumer and clinical hardware. Various models provided herein use voltage-time information from ECGs as inputs.

Accordingly, in some aspects of the invention, disclosed herein are methods comprising receiving voltage-time data of a subject, the voltage-time data comprising voltage data of a lead of an electrocardiogramanerating a feature vector from the voltage-time data; providing the feature vector to a pretrained learning system; and receiving from the pretrained learning system an indication of a cardiac condition of the subject. Generating the feature vector may comprise generating a spectrogram based on the voltage data of the plurality of leads.

In some embodiments, such methods further comprise receiving demographic information of the subject, wherein generating the feature vector comprises adding the demographic information to the feature vector. In some such embodiments, the method further comprises receiving genomic information of the subject. Generating the feature vector may comprise adding the genomic information to the feature vector. Without being bound by any particular methodology or theory, said genomic data may be derived from a biological sample that is derived from a patient predisposed to increased cardiovascular risk, e.g., family history or genetic and/or protein markers. In some such embodiments, the learning system comprises a convolutional neural network. Such convolutional neural networks may comprise at least one residual connection.

In some embodiments the voltage-time data of a subject is received from an electrocardiogram further embodiments, the voltage-time data of a subject is received from an electronic medical record.

In some embodiments, the method further comprises providing the indication to an electronic health record system for storage in a health record associated with the subject. In some embodiments, the method further comprises providing the indication to a computing node for display to a user.

In some embodiments of the methods disclosed herein, the feature vector comprises a temporal dimension. In some such embodiments, each of a plurality of columns corresponds to a timestamp. In some embodiments, the temporal dimension has a resolution of 500 Hz.

With reference now to FIG. 1, a system for detecting or otherwise predicting a cardiac condition is illustrated according to embodiments of the present disclosure. As outlined above, in various embodiments, patient information, including electrocardiogram (ECG) data, is provided to a learning system. Thus, aspects of the invention, as disclosed herein, also include a system comprising: an electrocardiogramprising at least lead; a computing node comprising a computer readable storage medium having program instructions embodied therewith, the program instructions executable by a processor of the computing node to cause the processor to perform a method comprising: receiving voltage-time data of a subject from the echocardiograph; generating a feature vector from the voltage-time data; providing the feature vector to a pretrained learning system; and receiving from the pretrained learning system an indication of a cardiac condition in the subject. Generating the feature vector may comprise generating a spectrogram based on the voltage data of the plurality of leads.

In some embodiments, such systems further comprise receiving demographic information of the subject, wherein generating the feature vector comprises adding the demographic information to the feature vector. In some such embodiments, the system further comprises receiving genomic information of the subject. Generating the feature vector may comprise adding the genomic information to the feature vector. Without being bound by any particular methodology or theory, said genomic data may be derived from a biological sample that is derived from a patient predisposed to increased cardiovascular risk, e.g., family history or genetic and/or protein markers. In some such embodiments, the learning system comprises a convolutional neural network. Such convolutional neural networks may comprise at least one residual connection.

In some embodiments the voltage-time data of a subject is received from an electrocardiogram further embodiments, the voltage-time data of a subject is received from an electronic medical record.

In some embodiments, the system further comprises providing the indication to an electronic health record system for storage in a health record associated with the subject. In some embodiments, the system further comprises providing the indication to a computing node for display to a user.

In some embodiments of the system disclosed herein, the feature vector comprises a temporal dimension. In some such embodiments, each of a plurality of columns corresponds to a timestamp. In some embodiments, the temporal dimension has a resolution of 500 Hz.

Patient data may be received from electronic health record (EHR) 101. An electronic health record (EHR), or electronic medical record (EMR), may refer to the systematized collection of patient and population electronically-stored health information in a digital format. These records can be shared across different health care settings. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information. EHR systems may be designed to store data and capture the state of a patient across time. In this way, the need to track down a patient's previous paper medical records is eliminated.

Electrocardiogram (ECG) data may be received directly from an electrocardiogra device 102. In an exemplary 12-lead ECG, ten electrodes are placed on the patient's limbs and on the surface of the chest. The overall magnitude of the heart's electrical potential is then measured from twelve different angles (leads) and is recorded over a period of time (usually ten seconds). In this way, the overall magnitude and direction of the heart's electrical depolarization is captured at each moment throughout the cardiac cycle. A single-lead ECG likewise records electrical potential over one angle.

Additional datastores 103, may include further patient information as set out herein. Suitable datastores include databases, flat files, and other structures known in the art. It will be appreciated that ECG data may be stored in an EHR for later retrieval.

It will also be appreciated that ECG data may be cached, rather than delivered directly to a learning system for further processing.

Learning system 104 receives patient information from one or more of EHR 101, ECG 102, and additional datastores 103. As set out above, in some embodiments, the learning system comprises a convolutional neural network. In various embodiments, the input to the convolutional neural network comprises voltage-time information an ECG, which in some embodiments is paired with additional patient information such as demographics or genetic information.

Learning system 104 may be pretrained using suitable population data as set out in the examples in order to produce an indication of a cardiac condition. In some embodiments, the indication is binary. In some embodiments, the indication is a probability value, indicating the likelihood of the cardiac condition given the input patient data.

In some embodiments, learning system 104 provides the indication of the cardiac condition for storage as part of an EHR. In this way, a computer-aided diagnosis is provided, which may be referred to by a clinician. In some embodiments, learning system 104 provides the indication of cardiac condition to a remote client 105. For example, a remote client may be a health app, a cloud service, or another consumer of diagnostic data. In some embodiments, the learning system 104 is integrated into an ECG machine for immediate feedback to a user during testing.

In some embodiments, a feature vector is provided to a learning system. Based on the input features, the learning system generates one or more outputs. In some embodiments, the output of the learning system is a feature vector.

In some embodiments, the learning system comprises an SVM. In other embodiments, the learning system comprises an artificial neural network. In some embodiments, the learning system is pre-trained using training data. In some embodiments training data is retrospective data. In some embodiments, the retrospective data is stored in a data store. In some embodiments, the learning system may be additionally trained through manual curation of previously generated outputs.

In some embodiments, the learning system, is a trained classifier. In some embodiments, the trained classifier is a random decision forest. However, it will be appreciated that a variety of other classifiers are suitable for use according to the present disclosure, including linear classifiers, support vector machines (SVM), or neural networks such as recurrent neural networks (RNN).

Suitable artificial neural networks include but are not limited to a feedforward neural network, a radial basis function network, a self-organizing map, learning vector quantization, a recurrent neural network, a Hopfield network, a Boltzmann machine, an echo state network, long short term memory, a bi-directional recurrent neural network, a hierarchical recurrent neural network, a stochastic neural network, a modular neural network, an associative neural network, a deep neural network, a deep belief network, a convolutional neural networks, a convolutional deep belief network, a large memory storage and retrieval neural network, a deep Boltzmann machine, a deep stacking network, a tensor deep stacking network, a spike and slab restricted Boltzmann machine, a compound hierarchical-deep model, a deep coding network, a multilayer kernel machine, or a deep Q-network.

In machine learning, a convolutional neural network (CNN) is a class of feed-forward artificial neural networks applicable to analyzing visual imagery and other natural signals. A CNN consists of an input and an output layer, as well as multiple hidden layers. The hidden layers of a CNN typically consist of convolutional layers, pooling layers, fully connected layers and normalization layers. Convolutional layers apply a convolution operation to the input, passing the result to the next layer. The convolution emulates the response of an individual neuron to stimuli. Each convolutional neuron processes data only for its receptive field.

A convolution operation allows a reduction in free parameters as compared to a fully connected feed forward network. In particular, tiling a given kernel allows a fixed number of parameters to be learned irrespective of image size. This likewise reduces the memory footprint for a given network.

A convolutional layer's parameters consist of a set of learnable filters (or kernels), which have a small receptive field, but extend through the full depth of the input volume. During the forward pass, each filter is convolved across the width and height of the input volume, computing the dot product between the entries of the filter and the input and producing a 2-dimensional activation map of that filter. As a result, the network learns filters that activate when it detects some specific type of feature at some spatial position in the input.

In an exemplary convolution, a kernel comprises a plurality of weights $w_1 \ldots w_9$. It will be appreciated that the sizes provided here are merely exemplary, and that any kernel dimension may be used as described herein. The kernel is applied to each tile of an input (e.g., an image). The result of each tile is an element of a feature map. It will be appreciated that a plurality of kernels may be applied to the same input in order to generate multiple feature maps.

Stacking the feature maps for all kernels forms a full output volume of the convolution layer. Every entry in the output volume can thus also be interpreted as an output of a neuron that looks at a small region in the input and shares parameters with neurons in the same feature map.

Convolutional neural networks may be implemented in various hardware, including hardware CNN accelerators and GPUs.

Figure 2:
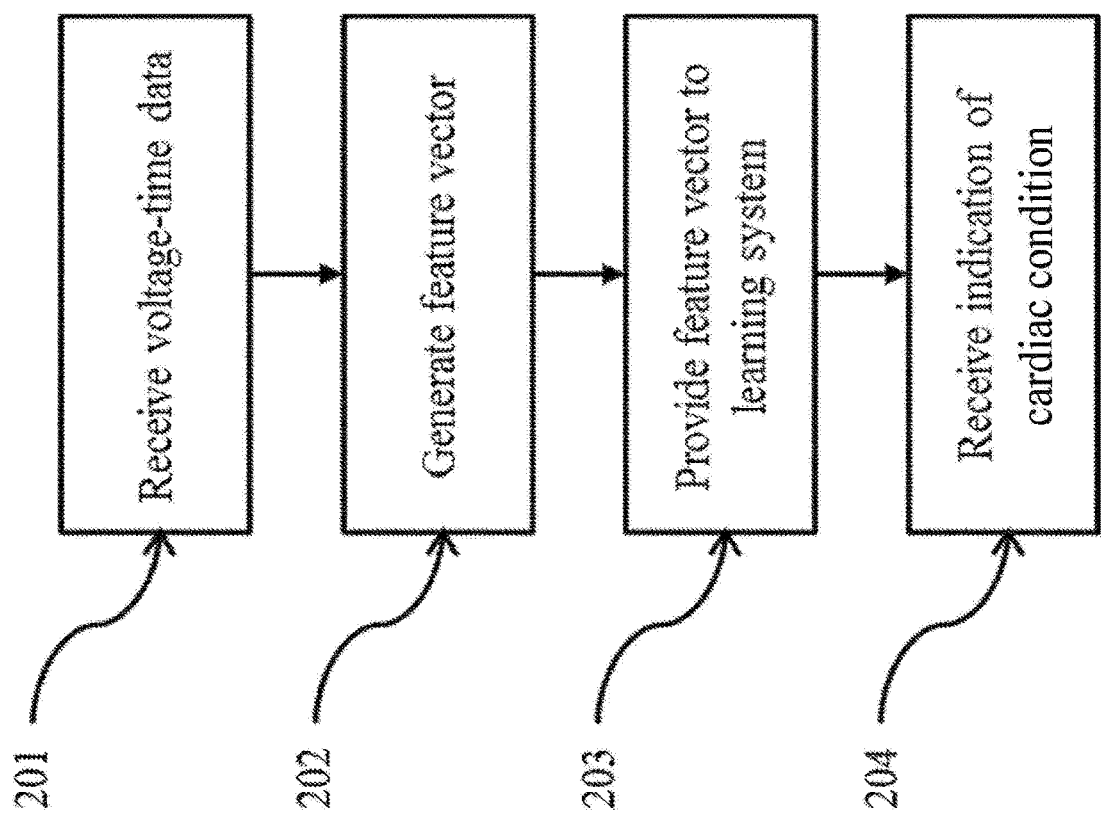
FIG. 2 is a flowchart illustrating a method of detecting or otherwise predicting a cardiac condition according to embodiments of the present disclosure.

Referring now to FIG. 2, a flowchart is provided illustrating a method of detecting or otherwise predicting a cardiac condition according to embodiments of the present disclosure. At 201, voltage-time data of a subject is received. The voltage-time data comprises voltage data of a plurality of leads of an electrocardiogram is generated from the voltage-time data. At 203, the feature vector is provided to a pretrained learning system. At 204, an indication of the cardiac condition in the subject is received from the pretrained learning system.

Figure 3:
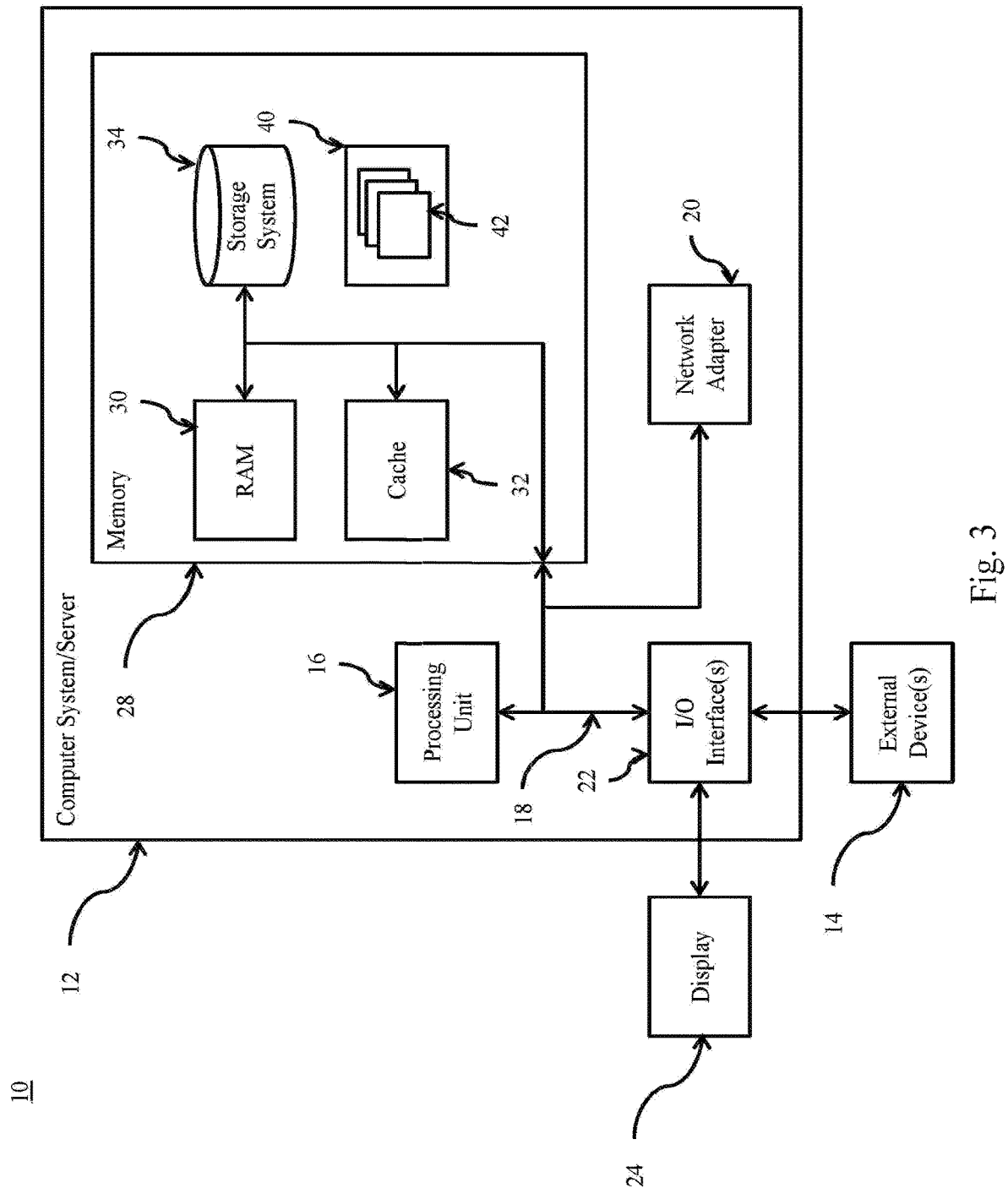
FIG. 3 depicts a computing node according to an embodiment of the present disclosure.

Referring now to FIG. 3, a schematic of an example of a computing node is shown. Computing node 10 is only one example of a suitable computing node and is not intended to suggest any limitation as to the scope of use or functionality of embodiments described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, Peripheral Component Interconnect Express (PCIe), and Advanced Microcontroller Bus Architecture (AMBA).

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiberoptic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

This specification describes how a system implemented as computer programs on one or more computers in one or more locations can perform a machine learning task on a neural network input derived from an ECG to generate a neural network output. For example, the system can be used for screening, diagnosis, or prognosis of (asymptomatic) cardiovascular diseases such as atrial fibrillation, hypertrophic cardiomyopathy, and left ventricular dysfunction by processing ECG data. As another example, the system can be used to estimate a person's sex, age, race, or a combination thereof by processing data describing the person's ECG.

A neural network receives an input and generates an output based on the received input and on values of the parameters of the neural network. The neural network may be composed of multiple levels, one or more of which may be layers of non-linear operations. An example of a neural network is a deep neural network with one or more hidden layers.

Different neural networks, e.g., neural networks with different parameter values, different model architectures, or both, may be used to process ECG data in different formats, different length, or collected using different hardware devices. For example, two neural networks with distinct parameter values typically generate different neural network outputs from one another, even though the inputs to the respective neural networks are derived from different ECG data describing a same person's ECG.

Figure 4:
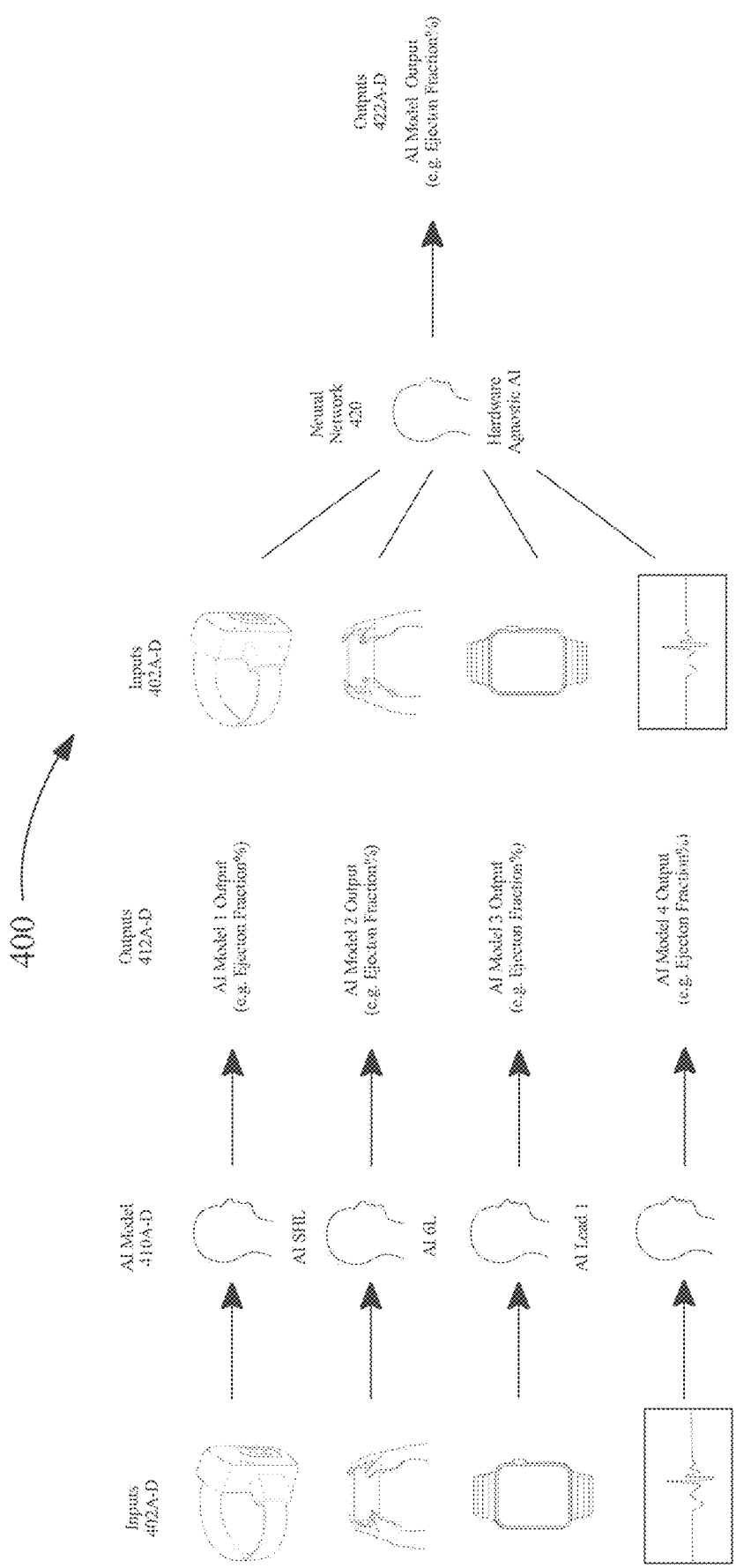
FIG. 4 depicts a schematic view of a system for processing lead-invariant ECG inputs according to embodiments of the present disclosure.

Referring to FIG. 4, a schematic view of a system for processing lead-invariant ECG inputs is provided.

In the example of FIG. 4, ECG data containing different numbers of leads and different formats (e.g., single-lead ECG data, 6-lead ECG data, mobile device-collected ECG data, and ECG data in image format) has been collected with respect to an individual, and four different machine-learning or artificial intelligence (AI) models (e.g., neural networks) 410A-D are respectively configured to process inputs 402A-D derived from the different ECG data in accordance current parameter values of the AI models to generate the outputs 412A-D. For example, each output can specify a predicted ejection fraction of the person. Because the AI models 110A-D have different parameter values, the outputs, e.g., predicted values of ejection fraction, are likely different from one another. This is shown on the left hand side of FIG. 4.

As shown on the right hand side of FIG. 4, the techniques described in this specification allows for implementation of a single hardware-agnostic neural network 420 that is configured and capable of processing any of inputs 402A-D that have been derived from different ECG data despite the different numbers of leads and formats of each of inputs 402A-D. Neural network 420 can thus use the same set of trained values of the weights and other parameters of the network 420 to generate an output (e.g., any of outputs 422A-D) according to a desired task (e.g., predicting or classifying a condition of the patient based on the patient's ECG).

Referring to FIG. 5, an exemplary invariant model architecture according to embodiments of the present disclosure is illustrated. In this example, the model is limited to fully convolutional. Any non-linearity is limited to the temporal axis. An average score among leads is used before the final non-linearity to maintain linear additional if information with additional leads.

FIG. 5 shows an example architecture of a hardware agnostic neural network. In particular, the hardware agnostic neural network includes a stack of one or more convolutional neural network layers and, in some cases, one or more non-linear activation layers that are collectively configured to process the neural network input to extract the temporal features (e.g., rather than spatial features) of the input. The extracted temporal features from ECG data collected using each single ECG lead are then combined, e.g., by using a pooling layer, and processed by a task sub-neural network to generate the neural network output. In this way, the neural network is easily configurable to process ECG data collected using different hardware devices, e.g., devices with different lead numbers, or in different time length. In some cases, the feature extraction sub-neural network is fully convolutional, i.e., does not include any fully-connected layers that have a fixed number of connections between the neurons. This allows for the hardware agnostic neural network to be able to accept ECG data in any of a variety of lengths. In some cases, the hardware agnostic neural network is invariant to ECG lead direction.

Figure 6:
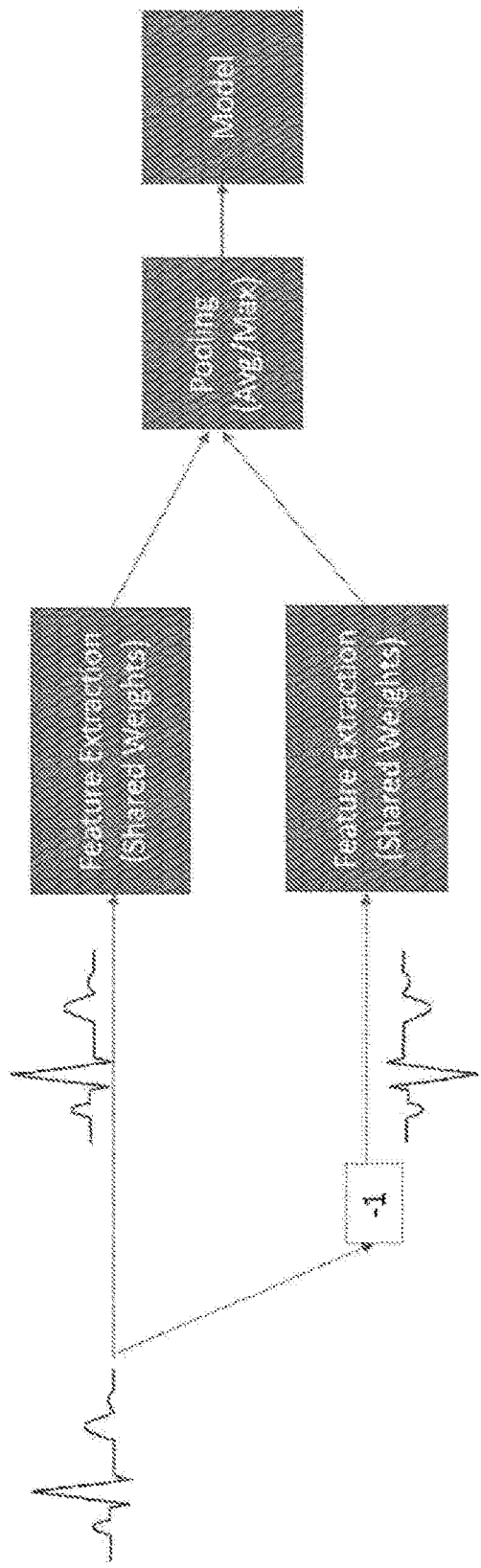
FIG. 6 depicts invariance of lead direction according to embodiments of the present disclosure.

As shown in FIG. 6, in these cases, the neural network can include two branches, one of which includes a transformation layer that applies a constant multiplier (e.g., multiply by −1) to the neural network input at this branch. The temporal features extracted from both branches are then combined and processed by the task sub-neural network to generate the neural network output. In some cases, the task sub-neural network is an attention-based neural network, e.g., a Transformer-based neural network, that includes one or more attention layers, e.g., self-attention layers or multi-head attention layers or both. Each attention layer is configured to receive an input sequence for the layer comprising a respective layer input at each of one or more positions, and thereafter generate an attended input sequence at least in part by applying an attention mechanism to the input sequence for the layer. The attended input sequence includes a respective attended layer input at each of the one or more positions.

Particular embodiments of the subject matter described in this specification can be implemented so as to realize one or more of the following advantages.

The system as described in this specification can be used to implement a neural network configured, e.g., through training, to perform a machine learning task such as a disease classification or prediction task on ECG data that is lead invariant and tolerant of various lead inputs and durations. In particular, once deployed, the neural network can accept ECG data in different formats, durations, or both than what has been used during training. For example, the neural network can process standard 12-lead ECG data to perform the machine learning task with sufficient accuracy, despite only having been trained on ECG data obtained from single-lead or multi-lead mobile or wearable devices, and without the need for retraining after deployment. Likewise, the neural network can process ECG data obtained from fewer leads than the number of leads presented to the neural network during training. It is therefore more computational resource-efficient to train and use the same neural network across a wide range of technical applications.

Unlike existing approaches such as missing lead interpolation, which can involve repeating ECG data collected by using a single lead twelve times, the neural network system described in this specification can generate the output based on computing a combination of temporal features extracted from ECG data collected by each single lead, thereby yielding more robust and predictable results.

The details of one or more embodiments of the subject matter of this specification are set forth in the accompanying drawings and the description below. Other features, aspects, and advantages of the subject matter will become apparent from the description, the drawings, and the claims.

Embodiments of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory program carrier for execution by, or to control the operation of, data processing apparatus. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them. The computer storage medium is not, however, a propagated signal.

The term "data processing apparatus" refers to data processing hardware and encompasses all kinds of apparatus, devices, and machines for processing data, including by way of example a programmable processor, a computer, or multiple processors or computers. The apparatus can also be, or further include, off-the-shelf or custom-made parallel processing subsystems, e.g., a GPU or another kind of special-purpose processing subsystem. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and pointing device, e.g, a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet. The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

Figure 7:
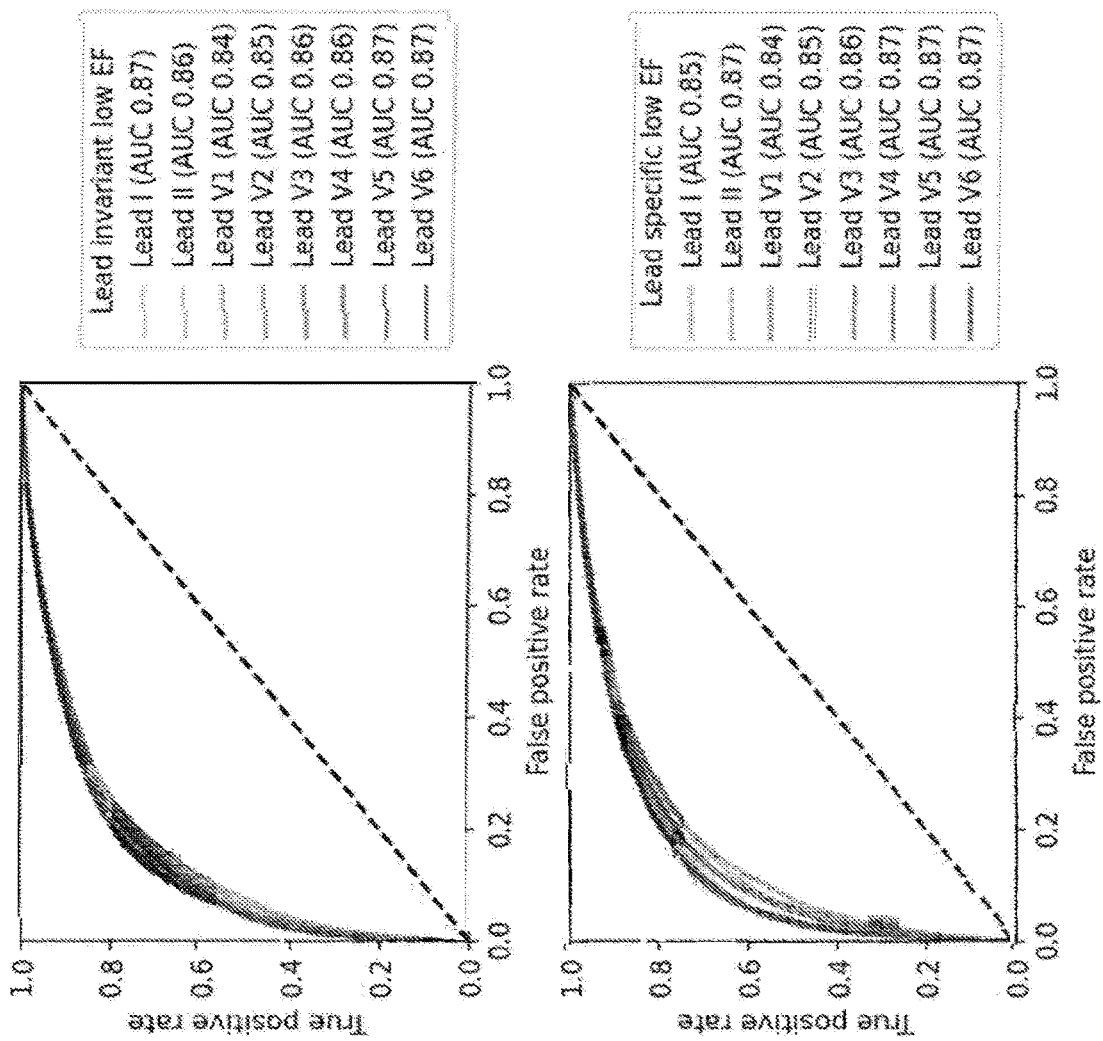
FIG. 7 depicts ROC curves for a lead invariant model (top) and a lead specific model (bottom) for EF classification according to embodiments of the present disclosure.

Referring to FIG. 7, ROC curves are provided for a lead invariant model (top) and a lead specific model (bottom) for EF classification.

Figure 8:
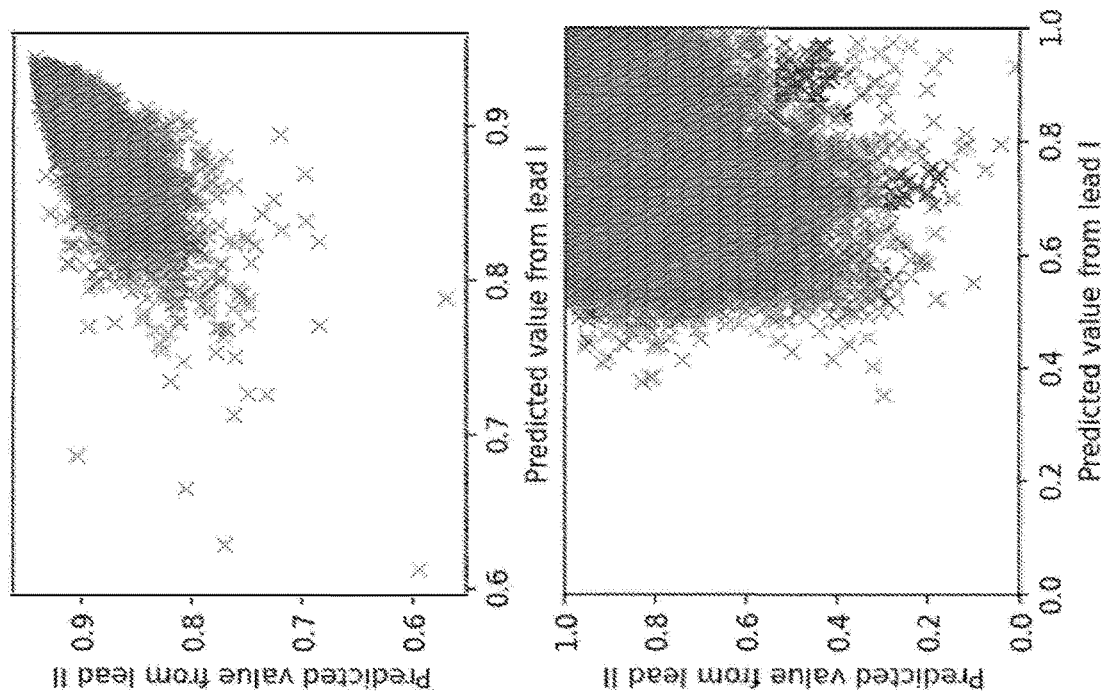
FIG. 8 depicts predicted values from a lead invariant model (top) and a lead specific model (bottom) for low EF classification according to embodiments of the present disclosure.

Referring to FIG. 8, predicted values are provided from a lead invariant model (top) and a lead specific model (bottom) for low EF classification.

ECG differ among different form factors in length and number of leads. For example: Apple Watch/Kardia IL—single lead for 30 seconds (mimic lead I); Eko Stethoscope—single lead for 15 seconds (non-specific lead); SHL—Twelve leads for 2.5 seconds in each lead; GE—Twelve leads for 10 seconds in each lead; PDFs—Twelve leads for 2.5 seconds in each lead and various additional leads. Using conventional methods, each input would require a different model due to the number of leads \lengths of ECG.

True hardware independence could enable FDA approval for a single model. A quick screen (dynamic range, sampling input, possible noise assessment) could identify suitable signals. The software as a medical device could then run independent of the hardware used to collect the ECG (irrespective of manufacturer, number of leads, duration of recording), and could also enable reading ECG PDFs. Since the same model is utilized and validated, would not need repeated FDA approvals.

Figure 9:
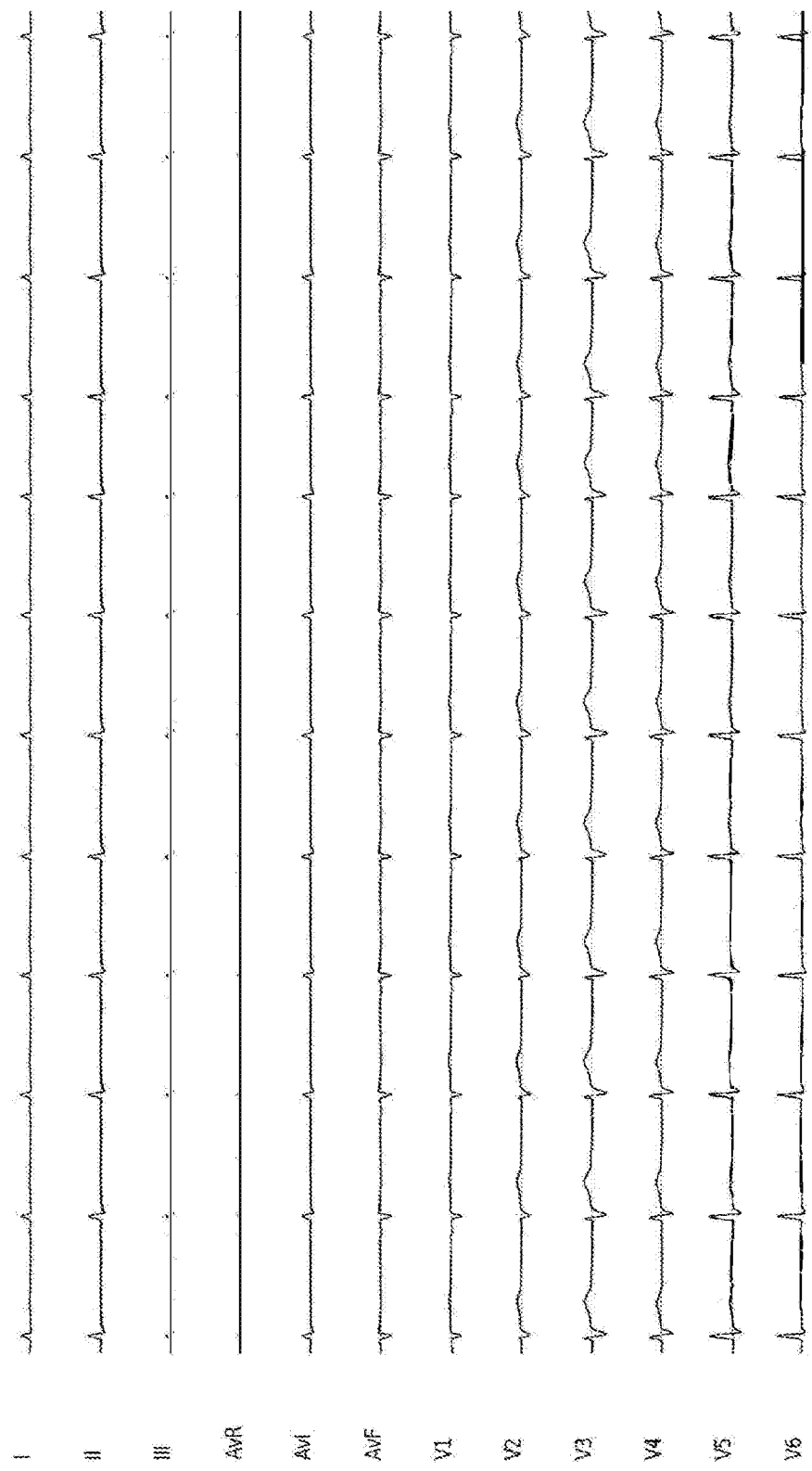
FIG. 9 illustrates an exemplary digital ECG according to embodiments of the present disclosure.

Referring to FIG. 9, an exemplary digital ECG is illustrated, showing 10 Seconds×12 leads.

Figure 10:
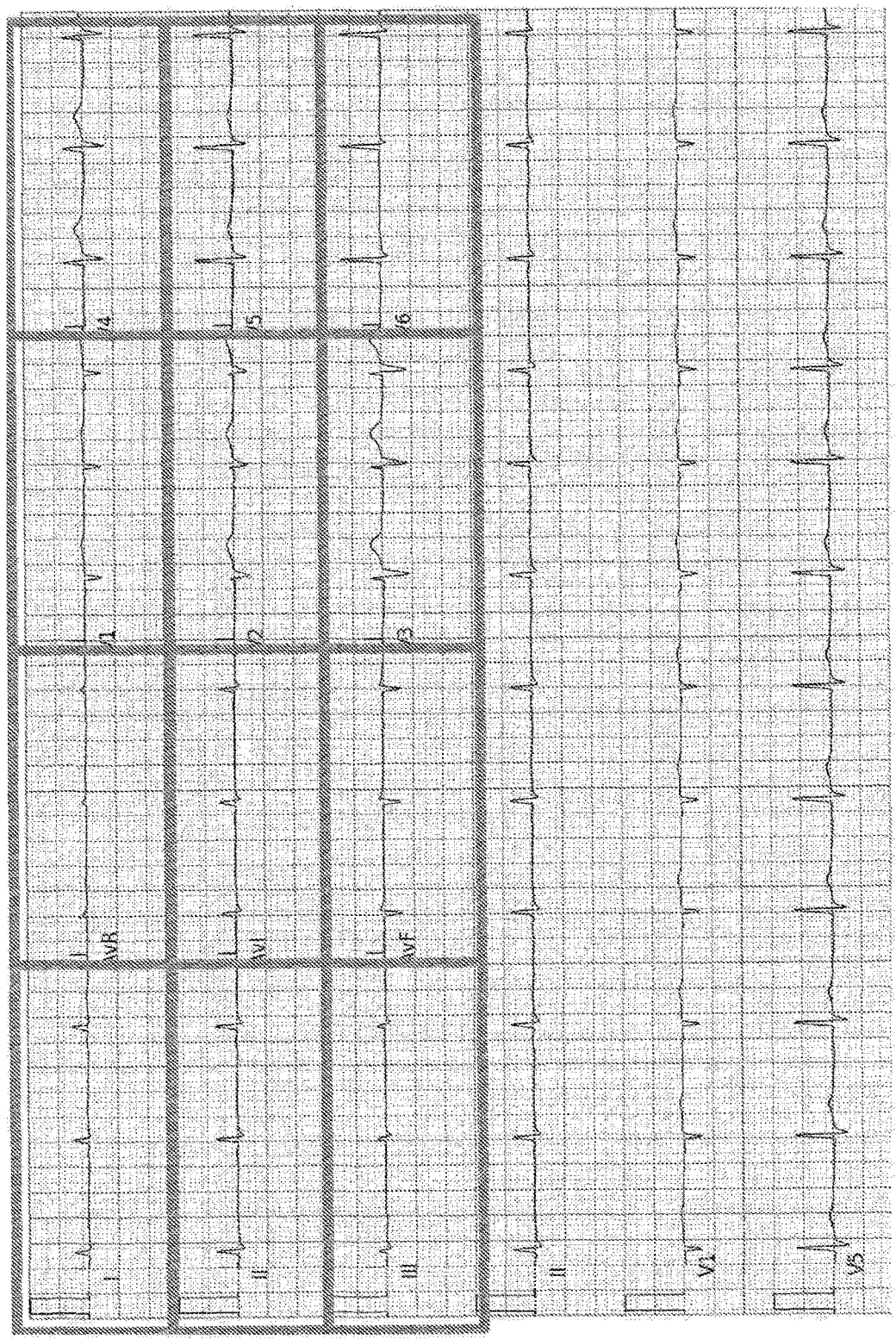
FIG. 10 illustrates an exemplary ECG-PDF according to embodiments of the present disclosure.

Referring to FIG. 10, an exemplary ECG-PDF is presented. The highlighted portions show 12 leads×2.5 seconds. Referring to the bottom rows, it will be seen that different presentations may be provided for these data.

Figure 11:
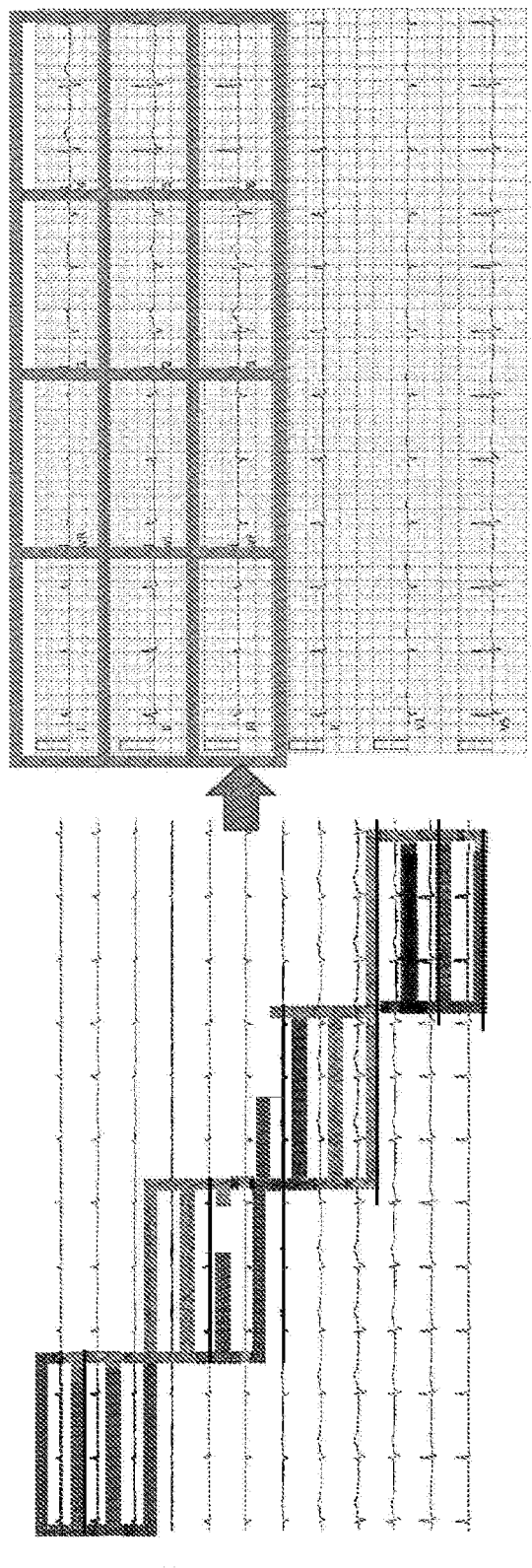
FIG. 11 illustrates a specific model for PDFs according to embodiments of the present disclosure.

Referring to FIG. 11, a specific model for PDFs is illustrated. In this example, each cluster of three leads (at four different times) are assembled into a PDF containing all 12 leads (at four different times) for training. In this way, a universal PDF may be generated, suitable for use in connection with the model of FIG. 4.

Figure 12:
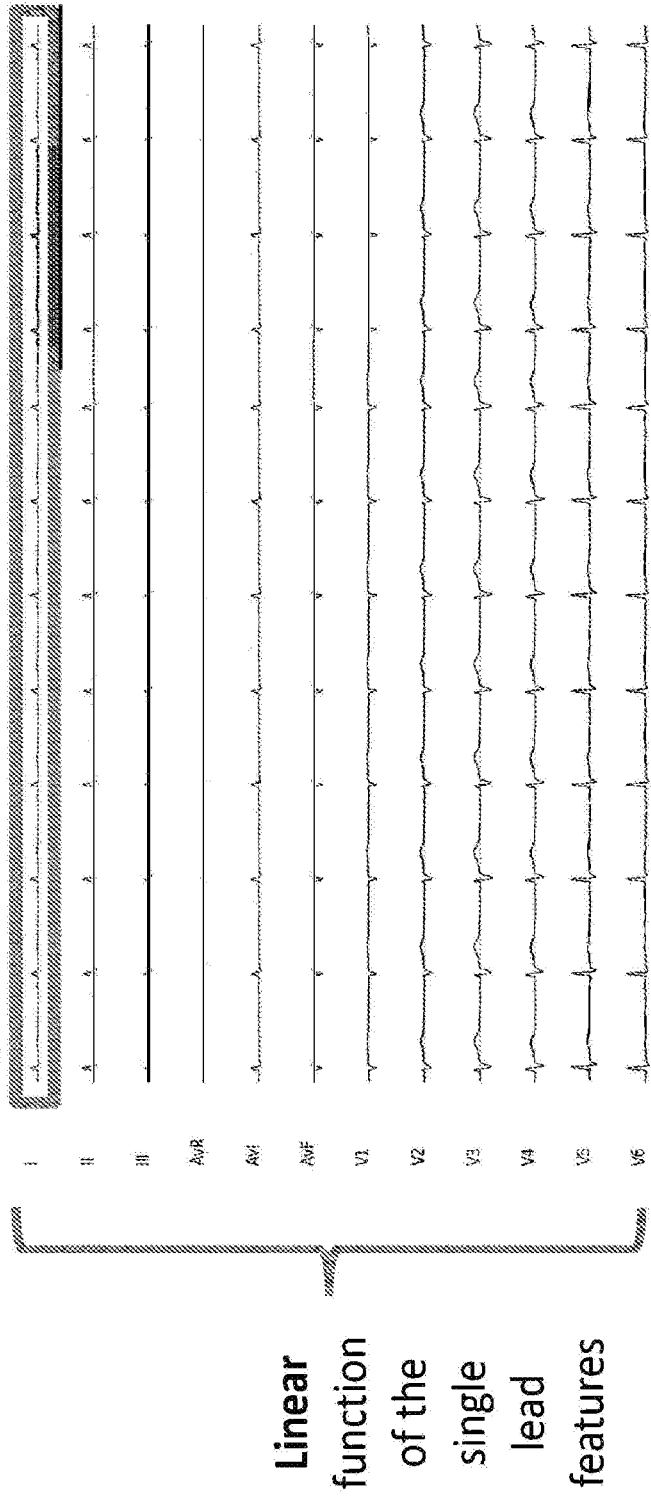
FIG. 12 illustrates nonlinear feature extraction according to embodiments of the present disclosure.

In the invariant model architecture depicted, nonlinear feature extraction is provided on the temporal axis as shown in FIG. 12.

Figure 13:
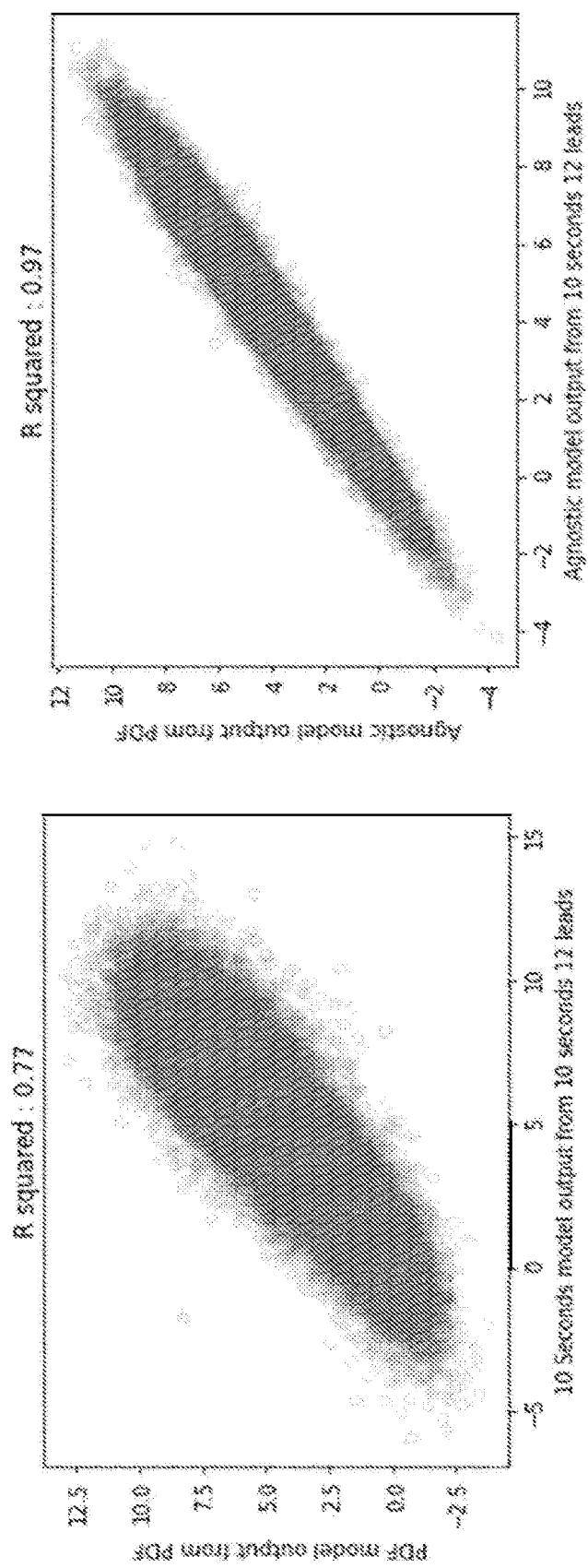
FIG. 13 illustrates results using 10 second data as compared to PDF data according to embodiments of the present disclosure.

FIG. 13 illustrates results using 10 second data as compared to PDF data. Full 10 seconds ECG using 10 seconds model yields AUC: 0.923. Full 10 seconds ECG using agnostic model yields AUC: 0.919. PDF version using PDF model yields AUC: 0.914. PDF using agnostic model yields AUC: 0.915.

Figure 14:
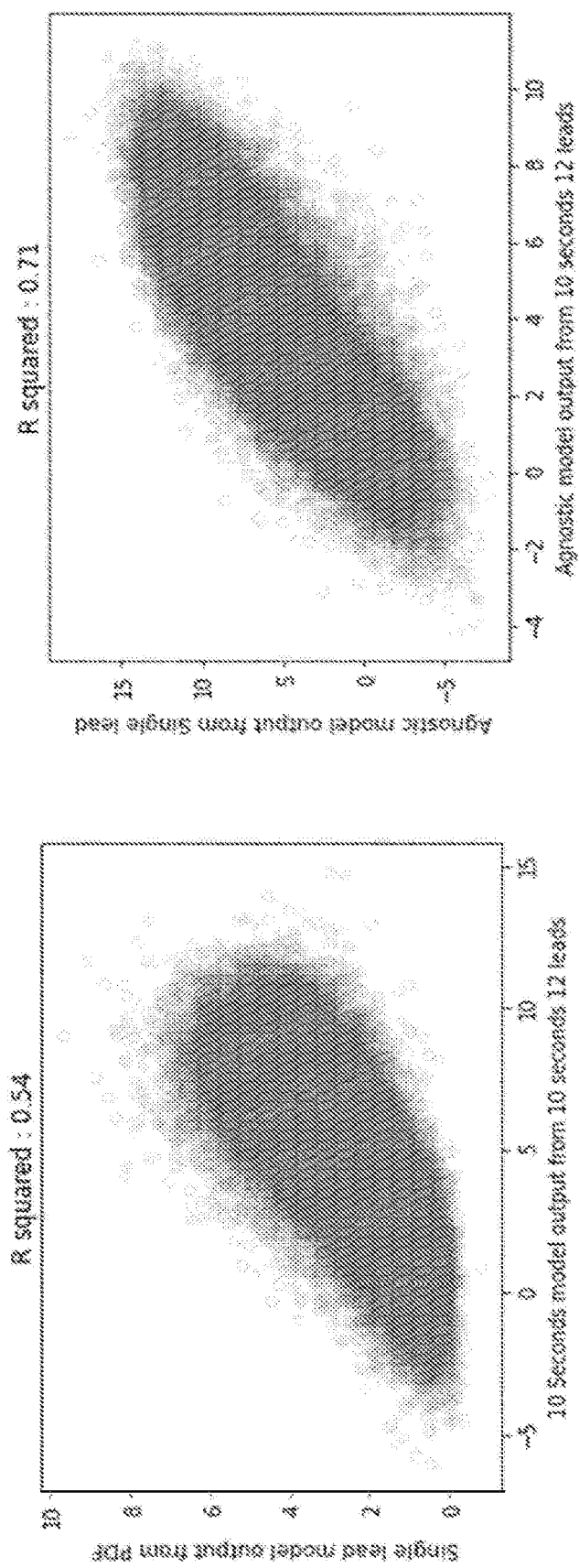
FIG. 14 illustrates results using 1/6 leads according to embodiments of the present disclosure.

FIG. 14 illustrates results using 1/6 leads. Single lead ECG using single lead model yields AUC: 0.87. Single lead ECG using agnostic model yields AUC: 0.89.

Figure 15:
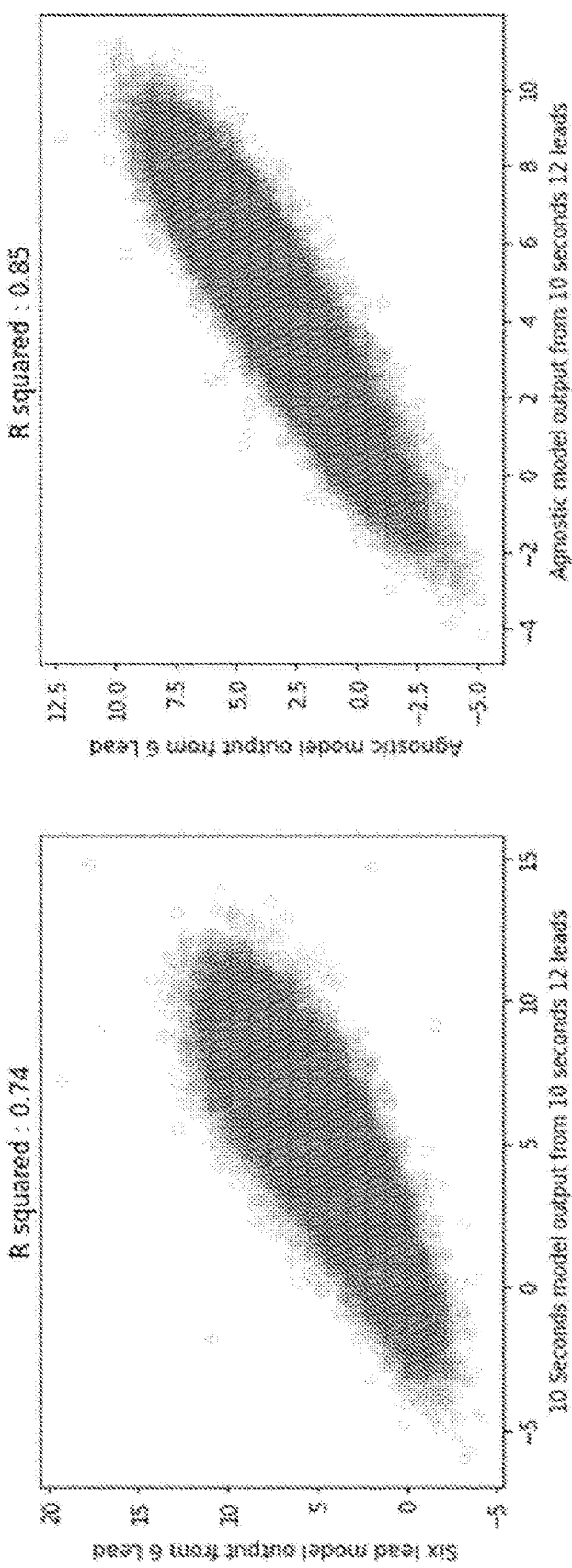
FIG. 15 illustrates results using 1/6 leads according to embodiments of the present disclosure.

FIG. 15 illustrates results using 1/6 leads. Six lead ECG using six lead model yields AUC: 0.917. Six lead ECG using agnostic model yields AUC: 0.90.

Figure 16:
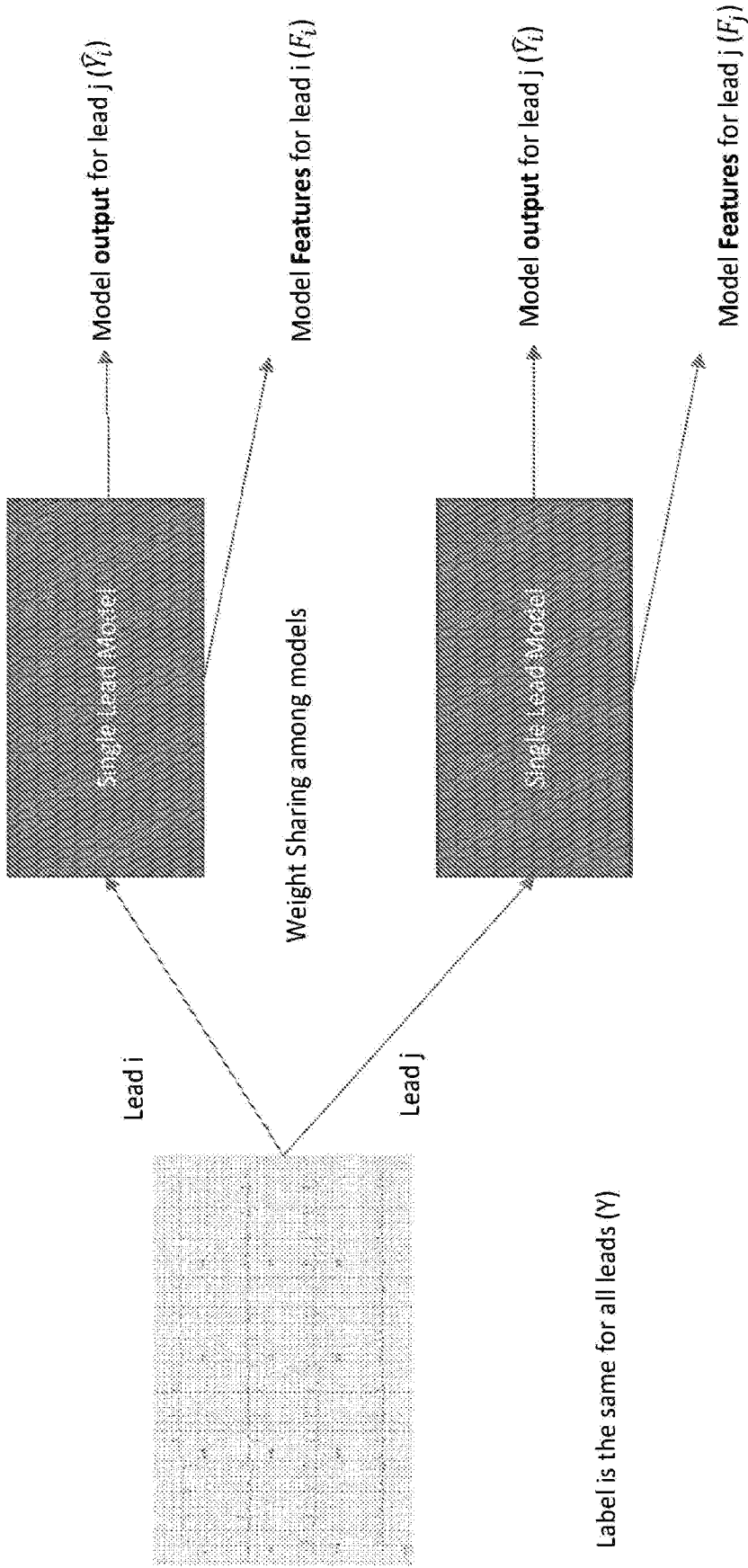
FIG. 16 illustrates an exemplary explicit model according to embodiments of the present disclosure.
Figure 17A:
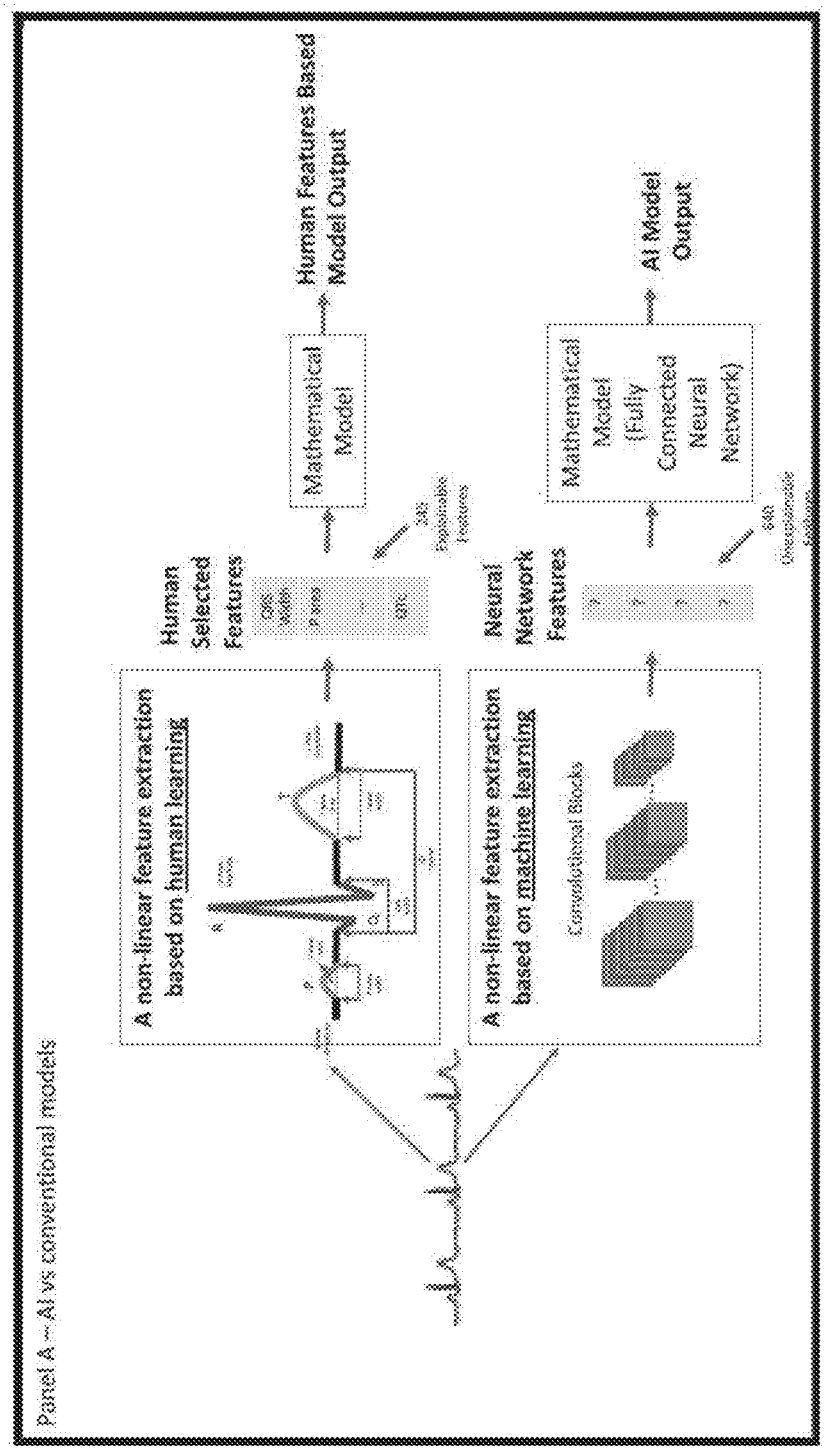
FIGS. 17A-D are diagrams of basic design of classifiers using human-selected or neural network-selected features, and an approach to quantify the relationship between these features according to embodiments of the present disclosure.
Figure 17B:
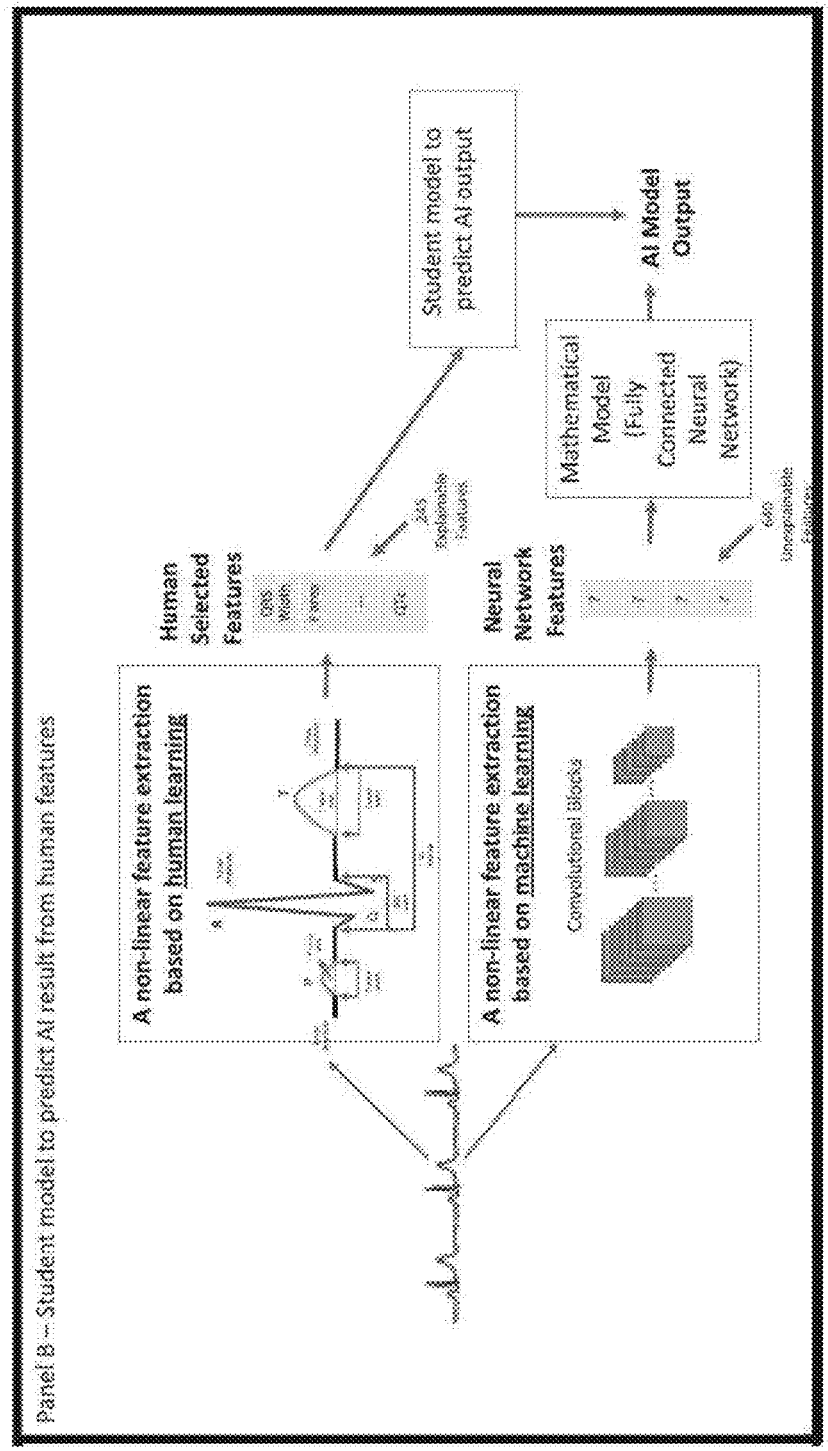
Figure 17C:
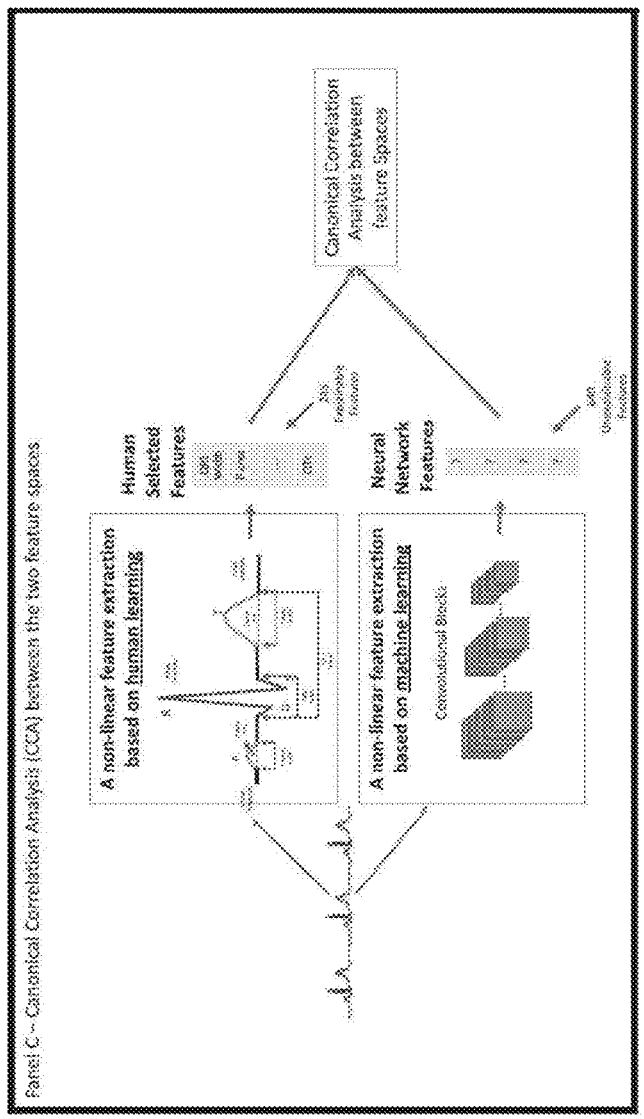
Figure 17D:
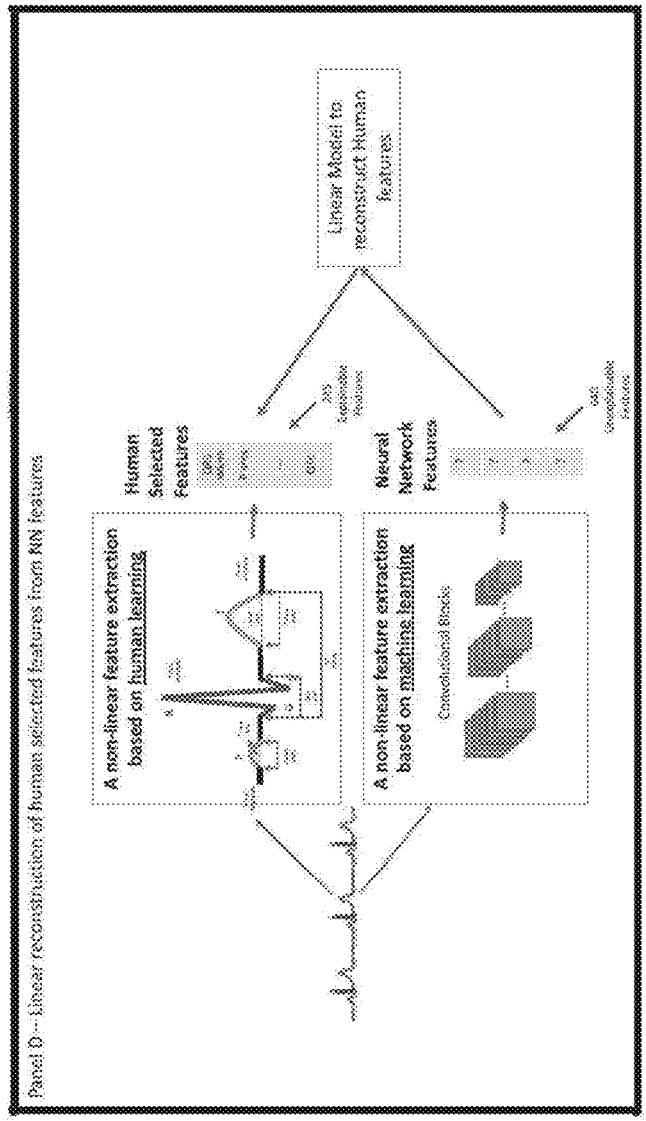

FIG. 16 illustrates an exemplary explicit model 1600 according to embodiments of the present disclosure. New loss function=BCE $(Y, Y_i)$+BCE$(Y, Y_j)$+$\alpha(|Y_j-Y_i|)$+$\beta(|F_i-F_j|)$ where BCE is the regular binary cross entropy between the model output to the label Alpha and Beta are the hyper parameters that control the tradeoff between the model overall accuracy and the lead invariance.

In one or more embodiments, the present disclosure may described exemplary illustrations of cardiac anatomy and electrocardiogram signals. The heart has four chambers. The upper chambers (the atria) are activated by the signal reflected in the electrocardiogram as the P-wave. The lower chambers (the ventricles) are rapidly activated resulting in the QRS complex; the relaxation of the ventricles (repolarization) is represented by the smoother T-wave. A number of human-selected features, such as the peak amplitude of the various waves, the areas and widths of the different waves, deviation from baseline, and other morphological characteristics have a known biological mechanism and associations with specific pathologies. It may be recognized that multiple medical conditions may affect any individual feature, and any individual condition may impacts multiple features. For diagnosis, clinicians may trained to recognize the most salient features associated with a given condition, while other changes, due to their small magnitude or variability are ignored. Human-crafted models may weigh-selected features to classify the absence or presence of a disease state, such as acute myocardial infarction, associated with the features of ST-segment elevation.

Referring now to FIG. 17, a diagram 1700 of basic design of classifiers using human-selected or neural network-selected features, and an approach to quantify the relationship between these features is described. For the purposes of this disclosure, a "reasonable explanation" is defined as the translation of the rules used by a model for output determination to a language that a human expert can understand and replicate. These rules may be specific to the problem one tries to solve. In order to define an explainable model for understanding (neural networks) NNs for ECG processing, domain-specific vocabulary of human-selected features and basic methods for explain-ability and correlation may be identified.

With continued reference to FIG. 17, The ECG may include a recording of the heart's electrical activity from the body's surface. Each individual myocyte may contain a resting negative electrical potential relative to the outside of the cell membrane due to the distribution of ions across it. Highly regulated voltage changes, controlled by membrane ion-channels, permit individual myocytes to depolarize, allowing electrical signals to propagate across the myocardial syncytium, which through electrical-mechanical coupling result in coordinated mechanical contraction. Each myocyte may then repolarize (recover its resting negative potential) in preparation for the impulse to follow. The ECG may include a summation in space and time of all of the individual myocyte voltage changes and depicts the progression of electrical activation through the cardiac chambers of an individual's heart. Since the progression of cardiac wave fronts may occur in three-dimensional space, the recording acquired from any given skin electrode may reflect the projection of the electrical vector at that particular point in space, so that a given signal may have a different appearance when recorded from different sites. Conversely, recording from multiple surface locations may permit characterization of the cardiac site or origin of a given impulse. In a 12-lead ECG, 12 leads are recorded. The electrical activity in each heartbeat may be divided into 5 main temporal waves (features), the P, Q, R, S and T waves. The P-wave may represents atrial depolarization, the Q, R and S waves (typically referred to as the QRS complex) may represent ventricular depolarization, and the T-wave may reflect ventricular repolarization.

With continued reference to FIG. 17, When the ECG is acquired during normal rhythm, the morphology of each complex may have substantial homology among beats, so that an averaged beat is often used for morphologic feature extraction. The human-engineered process of feature extraction from ECG is non-trivial and non-linear. It may entail selection of specific signal components (e.g. the ST-segment) which is useful if associated with specific conditions. In one or more embodiments, human-defined features may be extracted and stored by a MUSE cardiology information system. The MUSE cardiology information system may integrate, manage and streamline the flow of cardiac information, enabling delivery distribution and analysis. The system may begin with the detection of each QRS complex in a segment and selection of a window of time around it, aligning the windows using a fiducial point in the QRS and averaging the complexes to a single representative beat. The features may be extracted by finding the onset and offset of each component and identifying human-selected characteristics such as areas, maximum amplitudes, slopes, durations, and so on for each constitutive element, creating a descriptive vocabulary for signal characteristics. The Muse system may include a matrix of human-selected features that are automatically extracted from each lead in a 12-lead ECG.

With continued reference to FIG. 17, two previously described deep convolutional NN may be used which are trained to classify ECGs for two different tasks: classification of sex and estimation of age. Using these networks, experiments may be conducted with 100,000 ECG signals from the Mayo Clinic digital data vault collected between January 1994 and February 2017 with institutional review board approval. ECGs may be randomly selected from all-corners including cardiac and non-cardiac patients; 57.4% may be male, while the mean age may include 58.7±15.7 years. The cohort used for these may be selected in a similar way to the cohorts used to train and validate the original models we sought to explain; however, the current cohort is independent of the latter ones. Among the 100,000 ECG signals, N=50,000 may be used to train the student models (denoted as the student model training set) and N=50,000 may be used to evaluate the student models (denoted as the student model testing set).

In the training of the previous age and sex models, each ECG signal may be zero padded from 5000×12 (10 seconds sampled at 500 Hz) to 5120×12 (i.e. for each of the 12 leads, the padded signal length was 5120), and no additional inputs may be used. For the sex classification problem, labels of patient sex may be provided as binary variables (0/1 for female/male) and the predicted output for the testing data obtained values in [0,1] indicating the probability of being a male. For the age estimation problem, labels of patient ages between 18 and 100 may be provided and the predicted output for the testing data obtained values in [18,100].

The architecture of the age convolutional NN and the sex convolutional NN may be the same except for the final output layer's activation [linear for age regression and SoftMax (binary classification) for sex]. In both networks, the first component may include convolutional blocks, which reduce the dimension of each 5120×12 signal to 640. This may be the feature extraction component of the network as denoted in FIG. 17. The NN-selected features may be defined as the 640 outputs of the last convolutional layer. The next network component may be the mathematical model; in this case, fully connected layers that received the 640 features selected by the convolutional layers and manipulate them to obtain the desired output. Additionally, a total of 245 human-selected features derived from the median beat of each of the 100,000 ECGs may be extracted using the Muse database. Some of the features may be based on the morphology of a single lead and may be extracted for each lead separately, but others, such as intervals (QT, RR, QRS) may be calculated based on all 12 leads.

For the purposes of this disclosure, the following notations are used, where for brevity, there is no distinguishment between sex classification and age estimation, as their models may identical except for the final output layer's activation:

$X_{train}$, $X_{test}$ [N×640] are the student model training and testing matrices of NN features;
$Z_{train}$, $Z_{test}$ [N×245] are the student model training and testing matrices of human-selected features; and
$y_{train}$, $y_{test}$ N×1 are the student model training and testing output of the NN with the trained parameters.

The NN outputs may be used to train and test the student model and not the given in order explain the NN output rather than create human features-based models.

With Continued reference to FIG. 17, a secondary student model may be used and designed to predict the output of the NN using the human-selected features to explain the NN. For simplicity, a linear regression model may be used. That is, we defined a 245×1 vector w and a real number b and fit a standard least-squares linear regression model $y_{train}=Z_{train}\omega+b1_{N\times1}$ where $1_{N\times1}$ is an N×1 vector of ones. The corresponding $R^2$ statistic, which incorporated the testing data, was interpreted as the linear explainability score. It has values between 0 and 1, where 1 designates perfect linear explanation and 0 an irrelevant vocabulary for linear explanation. It was computed as follows:

$$R^2 = 1 - \|y_{test} - (Z_{test}\omega + b1_{N\times1})\|^2 / \|y_{test} - \overline{y_{test}}1_{N\times1}\|^2$$

where for a vector a, $\overline{a}$ and $\|a\|$ denote the mean and Euclidean norms, respectively.

A non-linear model may also be used to explain the output using the human-selected features. This model may use a fully connected network with two layers of 128 and 64 neurons and ReLU activation functions, followed by linear regression. The model may be trained using a small set of hyperparameters and internally validated on a subset of the training data. Using matrices of parameters $W_{245\times128}$ and $V_{128\times64}$, a vector $\omega$ of size 64×1 and a scalar b, the non-linear model may be expressed as $y_{train}$=(ReLU(ReLU$(Z_{train}\ W_{245\times128}V_{128\times64})\omega+b1_{N\times1}$. the following $R^2$ statistic may be used as the non-linear explainability score:

$$R^2 = 1 - \|y_{test} - f(Z_{test})\|^2 / \|y_{test} - \overline{y_{test}}1_{N\times1}\|^2$$

The difference between the non-linear and linear explainability scores may quantify the improved performance of a non-linear versus a linear model.

In one or more embodiments, canonical correlation analysis (CCA) may be used to assess the overall correlation between the spaces of the human selected and NN features. CCA searches for linear transformations of the two sets of variables that maximize the cross-correlation between the transformed sets. In one or more embodiment, correlations may be quantified between the rows of the N×640 and N×245 matrices $X_{test}$ and $Z_{test}$ that represent NN and human-selected features, respectively, and pursue CCA as follows. The mean of all rows of a matrix may be subtracted from each row of that, so the variables may be centered. For d=min (rank($X_{test}$), rank($Z_{test}$)), $T_1$ and $T_2$ of coefficients of linear transformations may be sought, with respective sizes 640×d and 245×d, such that $X_{test}T_1$ and $Z_{test}T_2$ maximize the Frobenius norm of their cross-correlation matrix. The singular values of this maximal cross-correlation matrix may be canonical correlation coefficients that may be computer as follows. Let $U_1$ and $U_2$ be the N×d matrices of left singular column vectors (arranged by descending order of singular values) of $X_{test}T_1$ and $Z_{test}T_2$. respectively. Then the canonical correlation coefficients are the singular values of the matrix $U_1^T U_2$. These numbers are between zero and 1, where higher numbers indicate higher correlation. Due to redundancies, one expects that many of these coefficients should be close to zero. However, existence of k coefficients sufficiently large, where k<d, indicate a sufficiently close k=dimensional subspaces of human-selected and NN features. In order to reliably assess the amount of shared information between the two feature spaces, a comparison may be made between the number of pairs with a high correlation coefficient discovered by CCA to the reduced number of features obtained by principal component analysis that explained most of the variance.

In one or more embodiments, single human-selected features may be represented as linear combinations of NN features. The ith training and testing student model human-selected features may be identified with the ith rows of the matrices $Z_{train}$ and $Z_{test}$, which may be denoted by $Z_i^{train}$ and $Z_i^{test}$ respectively. Linear regression may be used on $Z_i^{train}$ against the rows of $X_{train}$. That is, a 245×1 $\omega_i$ vector and a real number $b_i$ and fit a standard least-squares linear regression model $Z_i^{train}=X_{train}\ \omega_i+b_i1_{N\times1}$, where $1_{N\times1}$ is an N×1 vector of ones. The corresponding $R^2$ statistic, which incorporates the testing data, is interpreted as the linear explainability score. It has values between 0 and 1, where 1 designates perfect linear explanation and 0 an irrelevant vocabulary for linear explanation. It may be computed as follows:

$$R^2 = 1 - \|Z_i^{test} - (X_{test}\omega_i + b_i 1_{NX1})\|^2 / \|Z_i^{test} - \overline{Z_i^{test}} 1_{NX1}\|^2$$

For human-selected features that were extracted from each of the leads (e.g. T amplitude), the ability to reconstruct the averaged feature value across leads may also be tested.

To verify that the network ability to reproduce the human features is not derived from a simple correlation between the human-selected features and the patient age and sex, he corresponding $R^2$ statistics may be calculated as well as the area under the curve (AUC) for detecting the patient's sex using that single feature alone.

In one or more embodiments, p-values may not be reported in order to rely on strong model assumptions. Such models may not be clear in one or more settings and various obstacles may exist in determining them. As a result, it may be preferred to use methods that do not rely on model assumptions, such as CCA and $R^2$ statistics. For the same reason, multiple testing may be omitted as well.

In one or more embodiments, the output of the two NNs (age and sex) using human features via linear and non-linear student models may be predicted. The variance information may be quantified and explained by these models via their $R^2$ statistic. For example, $R^2$ of value 1 means that 100% of the NN outputs may be explained using human features. For age estimation, the linear student model may explain 57.1% of the variance ($R^2=0.571$). A non-linear student NN with two layers may explain 70.2% of the variance ($R^2=0.702$). The difference between the two (13.1%) may be evidence of the non-linear use of these features by the deep NN. In fact, the NN may use a similar non-linear model after its convolutional blocks.

For sex classification, the linear student model may explain 49.4% of the variance ($R^2=0.494$). The non-linear student model may explain 68.5% of the variance ($R^2=0.685$), where the difference between the non-linear and linear explainability (19.3%) may be even greater. Indeed, in one or more embodiments, a linear model is often less useful for a binary classification than continuous regression.

Figure 18:
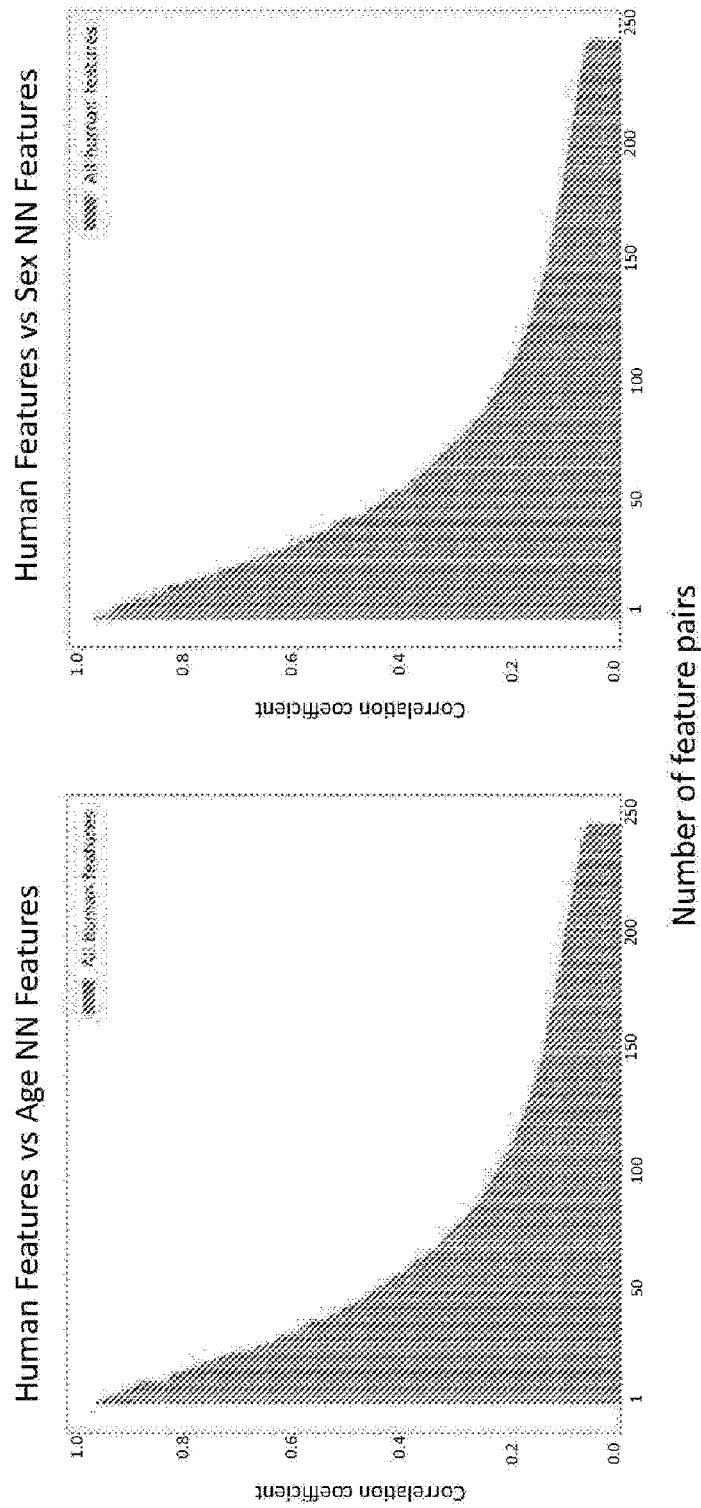
FIG. 18 is a graph of the canonical correlation coefficients for both sex classification and age estimation according to embodiments of the present disclosure.

Referring now to FIG. 18, A graph 1800 of the canonical correlation coefficients for both sex classification and age estimation is described. The canonical correlation analysis describes the correlation between the human-selected features and the age estimation neural network-selected features (left) and between the human-selected and neural network-selected features of the sex classification network (right). Each bar represents the canonical correlation coefficient between one pair of features from both spaces (neural network feature space and human-selected feature space). In an age model, 13 of the 245 feature pairs may have canonical correlation coefficients of 0.85 or higher and 8 of those may have a coefficient of 0.9 or higher. For the sex model, 15 of 245 of the feature pairs may have canonical correlation coefficients of 0.85 or higher and 10 of those had coefficients of 0.9 or higher. While 13 and 15 out of 245 may seem like a small number of pairs, it is important to note that human-selected features may be linearly correlated to one another due to biological reasons shown in FIG. 19.

Figure 19:
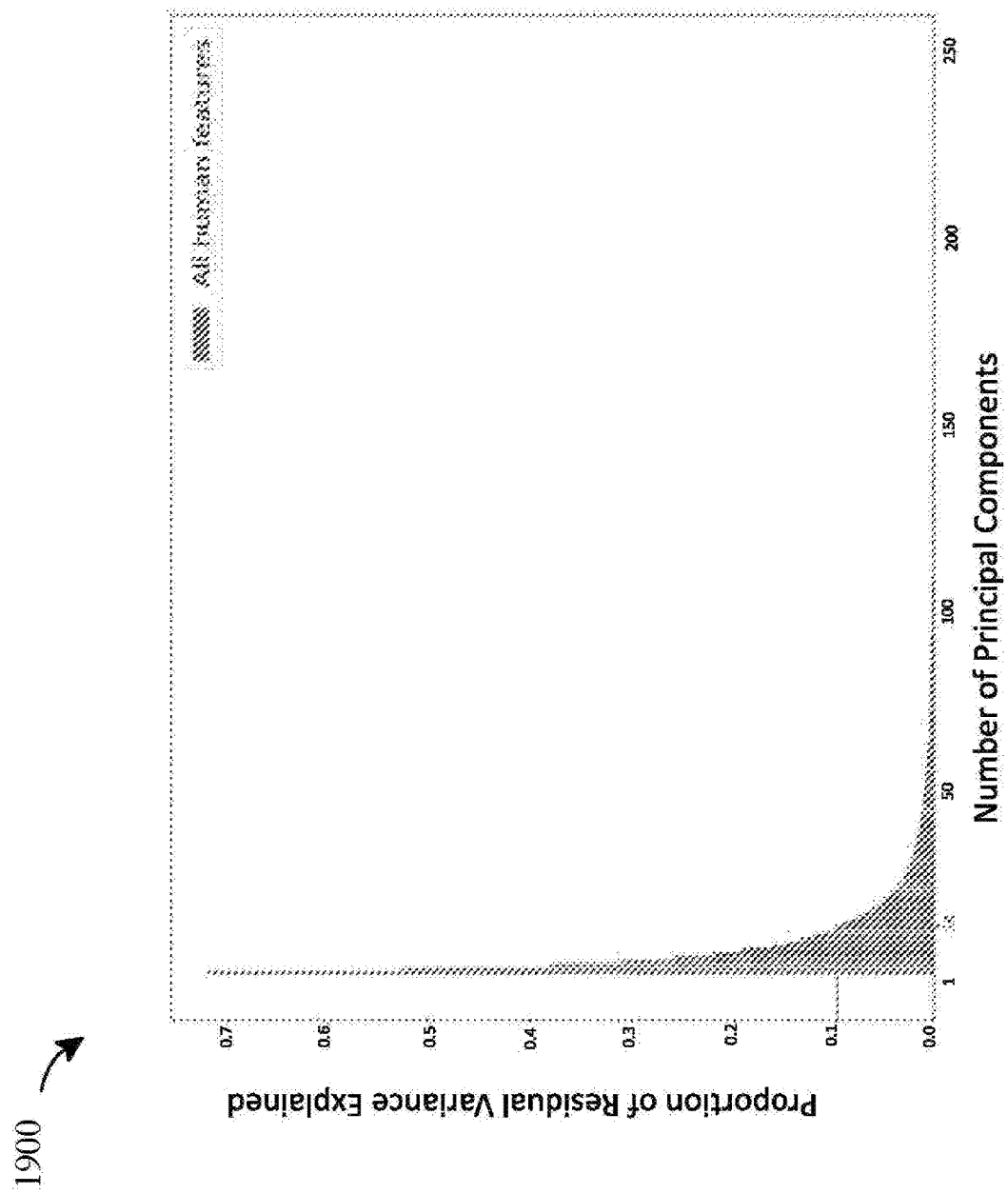
FIG. 19 is a graph of proportion of residual variance explained as a function of principal components is depicted according to embodiments of the present disclosure.

Referring now to FIG. 19, a graph 1900 of proportion of residual variance explained as a function of principal components is depicted. Since the human features have inherent biological correlations, principal component analysis may be used to quantify the number of unique features. As seen in the FIG. 14, 14 features MAY explain 90% of the information in the human-selected feature space.

Referring now to FIG. 20, a table 2000 for $R^2$ statistic as a measure of variance explainability for single human features in the two networks is described. To further understand the relationship between the two kinds of features, linear models may be created to reconstruct single human-selected features from NN features. In one or more embodiments, $R^2$ statistics may be reported as a measure of variance explainability for human features in the two networks (sex or age). If the feature is computed for each lead separately, and not derived from all 12 leads, then the table may report the maximal value of the $R^2$ statistics from all leads and the $R^2$ statistics of the average feature value across leads. In one or more embodiments, the $R^2$ statistics of all features including all leads, and the $R^2$ statistics between each human-selected feature and patient age and sex, as well as the AUC for detecting the patient's sex using that single feature alone. The feature with the highest correlation with output and highest AUC may be 'Maximum R Amplitude'; its $R^2$ statistic for age estimation is 0.13 and its AUC for detection of sex is 0.68.

With continued reference to FIG. 20 only the maximal $R^2$ values among leads and $R^2$ values of the averaged features across leads are reported, since the human features across leads may be correlated. Features that were derived from all 12 leads together are present as is (clearly, for these features the third column does not assign anything and the second and fourth columns assign the same value). The features are sorted according to a descending maximal $R^2$ value.

Figure 21:
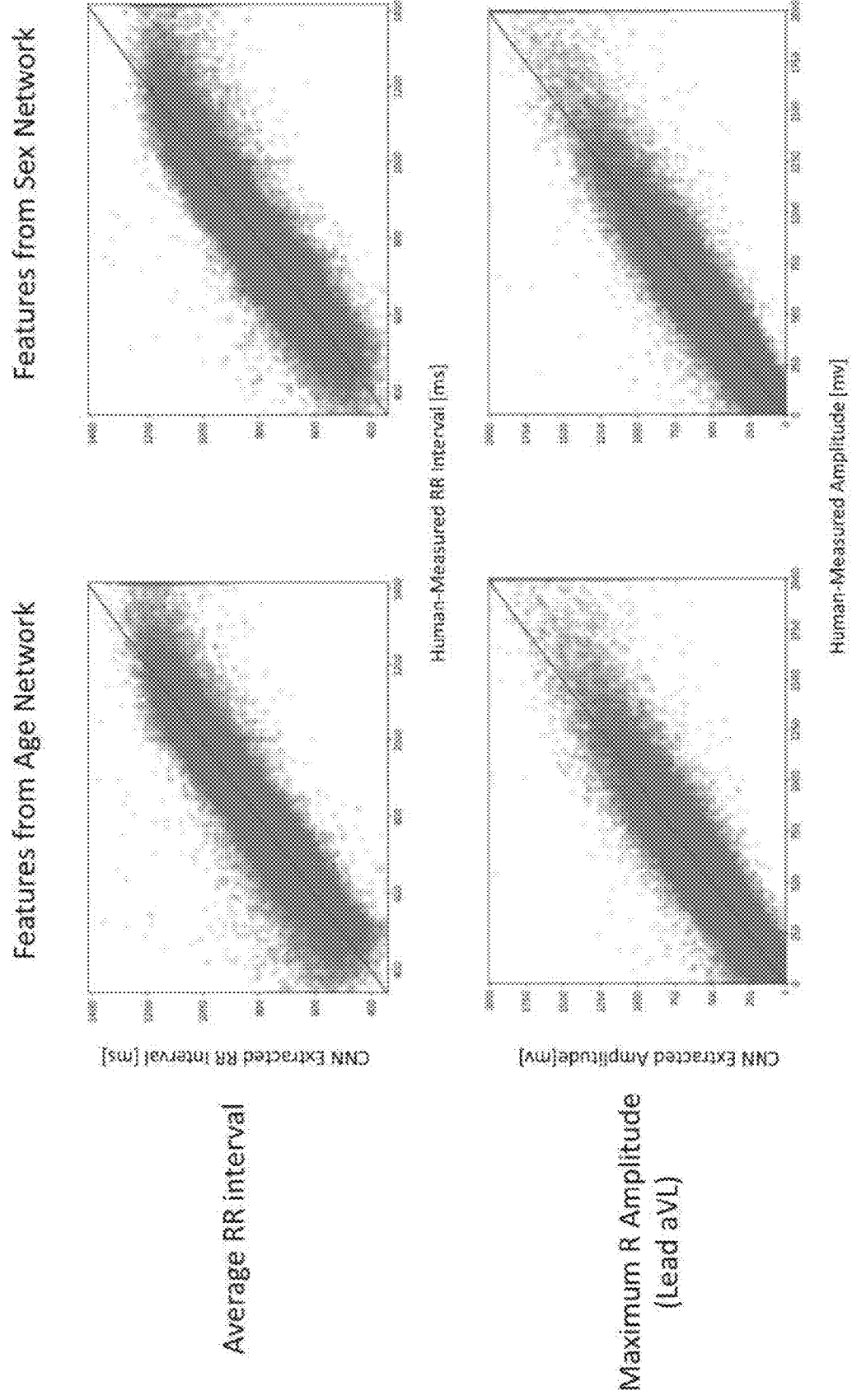
FIG. 21 is an illustration of strong correlation between each feature value (depicted on the x axis) and its reconstruction from the NN using the linear regression model (depicted on its y axis) for two features (average RR interval and maximal R amplitude) in both networks according to embodiments of the present disclosure.

Referring now to FIG. 21, an illustration 2100 of strong correlation between each feature value (depicted on the x axis) and its reconstruction from the NN using the linear regression model (depicted on its y axis) for two features (average RR interval and maximal R amplitude) in both networks is depicted. For an age estimation neural network feature, the feature with the highest $R^2$ statistic may be the patient heart rate (average RR interval) even though there may be no correlation between the patients' age and their heart rate ($R^2<0.001$). In addition, even though the age and sex networks were trained separately, each with a different objective, and had different NN feature spaces, when extracting the human-selected features from the two different NN feature spaces, in both cases the same set of features may have the same $R^2$ values.

With continued reference to FIG. 21, two examples of human-selected features may be reconstructed in a linear manner from the neural network feature space: age estimation neural network features 2104 and sex classification neural network features 2108. Even though the networks were trained separately, both networks may possess a similar ability to reconstruct specific human identifiable features, which are non-linear in nature (average RR interval in the upper panels and maximum R-wave amplitude in the lower panels).

Referring now to FIGS. 15-20, a system or method using may determine whether the features selected by NNs designed for ECG analysis are human understandable features. In one or more embodiments, systems and methods may further including asking whether the difference between the classification capabilities of NNs and humans stem from the use of different signal features, the non-linear nature of NNs, or both. In one or more embodiments, results may include results such as but not limited to: (i) NNs for ECG signals predominantly use features that are correlated with human understandable features; (ii) human-selected features, may however explain only part of the NN model output. For sex classification, a 70.2% variance explanation may be found with a non-linear model and for age estimation, it may be 68.5%. Thus, identification of novel features (signal components not part of the current vocabulary used to describe ECG signals) by the network may seem to contribute to the superior performance of NNs; (iii) the non-linear nature of NNs may also contribute to their superior performance. Indeed, the linear student models for both age estimation and sex classification may be able to explain less than the non-linear student models. In summary, NNs may predominantly use human-recognizable features, but then add additional non-human labelled features and non-linearity, accounting for their superior performance compared to traditional methods. Additionally, as the NN features are extracted without any specific feature engineering, errors in human feature creation may be eliminated and extraction time significantly shortened, as it does not involve manual review of each tracing.

The demonstrated ability to derive known ECG features with biological meaning from NN features in a linear way may mean that these features are not unique to human intelligence. Indeed, two different NNs (age and sex classifiers) may seem to utilize the same human-selected features without any a priori knowledge of what an ECG signal should look like, including the detection of features that are uncorrelated with the model labels. For example, and without limitation, the age estimation model may demonstrate strong ability to estimate the ECG heart rate from the NN features ($R^2=0.835$) with almost no correlation between the patient age and their heart rate ($R^2=0.0009$). This may supports a hypothesis that some of the NN features are natural in ECGs and are not specific to the outcome the network is trained to detect. Not all human-identified features might be used by the NNs. This might be considered a limitation, but it may also be another sign that each network underwent a meaningful learning process resulting in the selection of features that have a direct association with the classification task it was assigned.

Furthermore, there might not be a perfect explanation as to why the output of the model used the vocabulary of human-selected features, that is, the $R^2$ score was less than 1. There are three potential explanations for this finding. The first is that the NN found features that reflect components of the signals not defined by most humans, including features that are often described as 'gestalt'. These almost invisible features that appear to expert physicians might be hard to explain using any natural language and hard coded rules. The second is that the vocabulary used by humans to describe signal features may somehow be ambiguous and the definitions of some feature elements lack sufficient accuracy to provide robust classification. The last is that the network may have found false associations, for example, a feature that was present in the training set but was not generalizable or relevant for common instances. Such features represent a bias in the training set and might be exploited to permit a simple adversarial attack. To improve explainability in such cases one may apply adversarial training and possibly noise injection.

While a Ficus may be made on ECG analysis, and ECG-based features, a framework to extract and compare NN features, and human-selected features may be used using other means as well. For example, student models may be used and simple quantitative methods of correlating and explaining human-selected features using NN features. In one or more embodiments, systems and methods described herein may apply to other fields, where human-engineered features exist.

In one or more embodiments, systems and methods described herein may include systems and processes with frameworks using ECGs. The use of NNs to classify ECGs may allow for increased reliability due to the availability of large, well-annotated digital data sets. In addition, current networks have achieved human expert level capabilities with regards to reading ECG rhythms and have superseded humans in detecting a number of otherwise occult pathologies such as left ventricular dysfunction, hypertrophic cardiomyopathy, and subject age and sex based on the ECG alone. These are tasks humans may be incapable of, and understanding how these networks accomplish them might yield new medical knowledge. And lastly, ECG analysis has been performed for many years resulting in a very rich, biologically meaningful vocabulary of features that is carefully recorded. As the mechanism behind the features in the vocabulary may be known, translating the NN rules to these human features provides a direct link to the biology that drives the NN decision.

Understanding human-selected features that artificial intelligence (AI) models are looking at is important for the adoption of the technology in clinical medicine. Given the high stakes, the potential for novel or unexpected recommendations, the risk of implicit bias and false associations, and the possibility of legal liability, clinicians may be hesitant to respond to medical diagnoses or therapies proposed by NNs without a general understanding of the specific features or characteristics they process. The ability to explain predictive AI models may enhance the ability to improve their performance and to predict appropriate use cases for their adoption. Furthermore, as much as AI models may identify novel signal components in creating their classifications, new insights may be derived regarding the signal and its association with health and disease, leading to fundamentally novel insights into disease pathogenesis.

The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system for performing a machine learning task which is a regression task on a neural network input derived from electrocardiogram (ECG) data to generate a neural network output, the neural network input including representations of any number, n, of ECG leads from the ECG data, in which n is an integer in a set of integers from 1 to a pre-defined maximum number of ECG leads, m, the system comprising:
   one or more computers and one or more storage devices storing instructions that, when executed by the one or more computers, cause the one or more computers to perform one or more operations to implement a neural network configured to perform the machine learning task, the neural network comprising:

a feature extraction sub-neural network that is configured to process the neural network input to generate n feature extraction network outputs, each of the n feature extraction network outputs describing temporal features from a different one of the n ECG leads represented in the neural network input;

a feature fusing sub-neural network that is configured to process the n feature extraction network outputs generated by the feature extraction sub-neural network to generate a fused feature network output; and a task sub-neural network that is configured to process the fused feature network output to generate the neural network output.

2. The system of claim 1, wherein the feature extraction sub-neural network comprises one or more convolutional neural network layers configured to extract convolutional features from the neural network input.

3. The system of claim 2, wherein the feature extraction sub-neural network is configured to apply one or more non-linear feature extraction functions to the convolutional features extracted from the neural network input to extract the temporal features.

4. The system of claim 1, wherein the feature fusing sub-neural network is configured to apply a global mean or max pooling function to the n feature extraction network outputs generated by the feature extraction sub-neural network for the n ECG leads.

5. The system of claim 1, wherein the task sub-neural network comprises one or more attention neural network layers.

6. The system of claim 1, wherein the task sub-neural network comprises an output neural network layer that generates the neural network output.

7. The system of claim 6, wherein the output neural network layer is configured to apply a non-linear activation function to a layer input to the output neural network layer to generate the neural network output.

8. The system of claim 1, wherein the ECG data collected by using each ECG lead comprises analog data characterizing ECG signals.

9. The system of claim 1, wherein the ECG data collected by using each ECG lead comprises numerical data comprising numerical values specifying amplitudes of ECG signals.

10. The system of claim 1, wherein the ECG data collected by using each ECG lead comprises image data characterizing ECG signals.

11. The system of claim 10, wherein the image data characterizing the ECG signals is in pixel format, including TIFF, PNG, or PDF file type.

12. The system of claim 1, wherein the machine learning task is a classification task over a set of cardiovascular diseases.

13. The system of claim 1, wherein the regression task is a task for predicting readings or an individual's age, sex or race.

14. The system of claim 1, wherein the machine learning task is a generative task for generating text or numerical data that characterizes the ECG data.

15. The system of claim 1, wherein the instructions, when executed by the one or more computers, cause the one or more computers to train the neural network, wherein training the neural network comprises:

receiving a training input derived from ECG signals;

processing the training input using the neural network in accordance with current values of a plurality of parameters of the neural network to generate a training neural network output; and determining an update to the current values of the plurality of parameters of the neural network based on optimizing an objective function for the machine learning task.

16. The system of claim 1, further configured to perform the machine learning task on a plurality of neural network inputs derived from different electrocardiogram (ECG) data to generate the neural network output, wherein the instructions that, when executed by the one or more computers, cause the one or more computers to, for each of the plurality of neural network inputs:

process the neural network input using the feature extraction sub-neural network and the feature fusing sub-neural network to generate a respective fused feature network output;

determine a combined intermediate neural network output based on the respective fused feature network outputs; and process the combined intermediate neural network output using an output neural network layer of the task sub-neural network to generate the neural network output.

17. A method of performing a machine learning task which is a regression task on a neural network input derived from electrocardiogram (ECG) data to generate a neural network output, the neural network input including representations of any number, n, of ECG leads from the ECG data, in which n is an integer in a set of integers from 1 to a pre-defined maximum number of ECG leads, m, the method comprising:

processing, using one or more computers and a feature extraction sub-neural network, the neural network input to generate n feature extraction network outputs, each of the n feature extraction network outputs describing temporal features from a different one of the n ECG leads represented in the neural network input;

processing, using the one or more computers and a feature fusing sub-neural network, the n feature extraction network outputs generated by the feature extraction sub-neural network to generate a fused feature network output; and processing, using the one or more computers and a task sub-neural network, the fused feature network output to generate the neural network output.

18. The method of claim 17, further comprising training the neural network, wherein training the neural network comprises:

receiving a training input derived from ECG signals;

processing the training input using the neural network in accordance with current values of a plurality of parameters of the neural network to generate a training neural network output; and determining an update to the current values of the plurality of parameters of the neural network based on optimizing an objective function for the machine learning task.

19. The method of claim 17, wherein the machine learning task is a generative task for generating text or numerical data that characterizes the ECG data.

* * * * *